(12) United States Patent
Adams et al.

(10) Patent No.: US 11,877,888 B2
(45) Date of Patent: Jan. 23, 2024

(54) ULTRASOUND PROBE WITH AN INTEGRATED NEEDLE ASSEMBLY AND A COMPUTER PROGRAM PRODUCT, A METHOD AND A SYSTEM FOR PROVIDING A PATH FOR INSERTING A NEEDLE OF THE ULTRASOUND PROBE

(71) Applicant: Dandelion Technologies LLC, Vero Beach, FL (US)

(72) Inventors: Paul Adams, Vero Beach, FL (US); Christopher Vetter, Dublin, OH (US); Michael Andrew Holtman, McLean, VA (US)

(73) Assignee: DANDELION TECHNOLOGIES LLC, Vero Beach, FL (US)

( * ) Notice: Subject to any disclaimer, the term of this patent is extended or adjusted under 35 U.S.C. 154(b) by 0 days.

(21) Appl. No.: 18/164,294

(22) Filed: Feb. 3, 2023

(65) Prior Publication Data

US 2023/0181153 A1    Jun. 15, 2023

Related U.S. Application Data

(63) Continuation of application No. 18/162,278, filed on Jan. 31, 2023, which is a continuation-in-part of application No. 17/410,301, filed on Aug. 24, 2021, now Pat. No. 11,701,082, which is a continuation of
(Continued)

(51) Int. Cl.
*A61B 8/08* (2006.01)
*A61B 8/00* (2006.01)
*A61B 17/34* (2006.01)
*A61B 90/00* (2016.01)

(52) U.S. Cl.
CPC .......... *A61B 8/0841* (2013.01); *A61B 8/4254* (2013.01); *A61B 8/4444* (2013.01); *A61B 8/483* (2013.01); *A61B 8/5253* (2013.01); *A61B 2017/347* (2013.01); *A61B 2017/3413* (2013.01); *A61B 2090/067* (2016.02)

(58) Field of Classification Search
None
See application file for complete search history.

(56) References Cited

U.S. PATENT DOCUMENTS

| 7,846,103 B2 | 12/2010 | Cannon, Jr. et al. |
| 11,129,588 B2 | 9/2021 | Adams et al. |

(Continued)

*Primary Examiner* — Yi-Shan Yang
(74) *Attorney, Agent, or Firm* — Sterne, Kessler, Goldstein & Fox P.L.L.C.

(57) ABSTRACT

Systems and methods for providing guidance to an operator of an ultrasound device that comprises an ultrasound probe housing that contains a plurality of probes. In embodiments, images of inside a body of a patient generated in accordance with reflected ultrasonic waves from the probes are received, the images are processed to identify a needle that has been inserted into the body of the patient, and a notification to the operator is generated based on one or more of a distance or direction of the needle relative to a location of an anatomical part also identified by processing of the images, a distance or direction of the needle relative to an internal target body location also identified by processing of the images, or a distance or direction of the needle relative to a desired path of the needle also identified by processing of the images.

21 Claims, 25 Drawing Sheets

Related U.S. Application Data application No. 16/445,355, filed on Jun. 19, 2019, now Pat. No. 11,129,588.

(56) References Cited

U.S. PATENT DOCUMENTS

| | | | |
|---|---|---|---|
| 2003/0179445 A1* | 9/2003 | Maenle | G02B 21/34 |
| | | | 359/368 |
| 2006/0241368 A1 | 10/2006 | Fichtinger et al. | |
| 2007/0129686 A1 | 6/2007 | Daily et al. | |
| 2011/0125022 A1 | 5/2011 | Lazebnik | |
| 2012/0296213 A1 | 11/2012 | Mauldin, Jr. et al. | |
| 2013/0066192 A1 | 3/2013 | Sarvestani et al. | |
| 2013/0102891 A1* | 4/2013 | Binnekamp | A61B 6/02 |
| | | | 600/7 |
| 2013/0131501 A1 | 5/2013 | Blaivas et al. | |
| 2013/0178789 A1* | 7/2013 | Mackool | A61B 90/37 |
| | | | 604/22 |
| 2013/0345718 A1* | 12/2013 | Crawford | A61B 5/061 |
| | | | 606/130 |
| 2014/0276081 A1 | 9/2014 | Tegels | |
| 2015/0112200 A1 | 4/2015 | Oberg et al. | |
| 2015/0223774 A1 | 8/2015 | Ikeda et al. | |
| 2016/0008057 A1* | 1/2016 | Peppou | A61B 18/02 |
| | | | 600/478 |
| 2016/0022309 A1 | 1/2016 | Allaway | |
| 2016/0374644 A1 | 12/2016 | Mauldin, Jr. et al. | |
| 2017/0020558 A1 | 1/2017 | Xu et al. | |
| 2018/0000446 A1* | 1/2018 | Lu | A61B 8/587 |
| 2018/0161502 A1 | 6/2018 | Nanan et al. | |
| 2019/0125470 A1 | 5/2019 | Moskowitz et al. | |
| 2020/0016373 A1 | 1/2020 | Hulvershorn et al. | |
| 2020/0030044 A1* | 1/2020 | Wang | G06F 3/04815 |
| 2020/0187981 A1 | 6/2020 | Tian et al. | |
| 2020/0397399 A1 | 12/2020 | Adams et al. | |
| 2021/0259660 A1* | 8/2021 | Bharat | G06T 7/0012 |
| 2021/0378628 A1 | 12/2021 | Adams et al. | |
| 2021/0386397 A1 | 12/2021 | Adams et al. | |
| 2021/0393234 A1 | 12/2021 | Adams et al. | |
| 2022/0000446 A1 | 1/2022 | Adams et al. | |
| 2022/0000565 A1* | 1/2022 | Gururaj | A61B 17/34 |
| 2022/0008033 A1 | 1/2022 | Adams et al. | |
| 2022/0047240 A1 | 2/2022 | Adams et al. | |

* cited by examiner

ULTRASOUND PROBE WITH AN INTEGRATED NEEDLE ASSEMBLY AND A COMPUTER PROGRAM PRODUCT, A METHOD AND A SYSTEM FOR PROVIDING A PATH FOR INSERTING A NEEDLE OF THE ULTRASOUND PROBE

CROSS-REFERENCE TO RELATED APPLICATIONS

This application is a continuation of U.S. patent application Ser. No. 18/162,278, filed Jan. 31, 2023, which is continuation-in-part of U.S. patent application Ser. No. 17/410,301, filed Aug. 24, 2021, which is a continuation of U.S. patent application Ser. No. 16/445,355, filed Jun. 19, 2019. The entirety of each of these applications is incorporated by reference herein.

FIELD OF THE INVENTION

Embodiments of the present invention generally relate to application of ultrasonic waves in medical procedures and more particularly to an ultrasound probe with an integrated needle assembly and a computer program product, a method and a system for providing a path for inserting a needle of the ultrasound probe.

BACKGROUND ART

Procedures that require needle penetration are some of the most common medical procedures, yet remain relatively unchanged since their inception in 1891. In a typical scenario, a practitioner uses palpation of landmarks, such as the iliac crests and the spinous processes, to guide location of a needle during a blind procedure. Examples of such procedures include lumbar puncture (LP), epidural and spinal injections, and spinal nerve blocks. Failure rate of one of the most common medical procedures, lumbar puncture, however, is about 20% owing to the difficulty of identifying landmarks and the inability to visualize the location and trajectory of the needle. This rate is expected to increase as obesity increases in the global population. While ultrasound has been used to aid in the identification of structural landmarks, needle insertion continues to be an obstructed or blind procedure without significant improvement in success rates with using static ultrasound. Failure of a bedside lumbar puncture consequently leads to a fluoroscopic lumbar puncture which results in increased cost, unnecessary inpatient admissions and delay in patient care. Additionally, pain control and anesthesia has increasingly included local and regional nerve blocks. These procedures can use either landmarks or are limited to two-dimensional (2D) ultrasound, which limits the number of providers choosing this method due to the high initial skill required for a successful procedure. For example, femoral nerve blocks are increasingly being utilized to decrease the need for opiate pain control after hip fractures, which are proven to have improved pain control and decrease adverse events.

Several recent approaches are meant to address the above mentioned problems. But each approach continues to have multiple system or use limitations. For example, certain systems include ultrasound devices with an attached needle. These devices, however, are limited in function at least by the location or attachment of the needle away from the ultrasound transducer itself such that the needle is outside of the field of view provided by the ultrasound transducers. Other devices provide a needle that has restricted movement yielding inadequate procedural flexibility. Additionally, other certain available devices provide inadequate image viewing, such as with 2D imaging, that make needle tracking or visualization more difficult for the medical practitioner. These systems also suffer from the inability to provide a predicted optimum path within the patient for needle travel. Obstructed image viewing of the needle path and inability to predict the path of the needle leads to procedure failure. Overall, there remains an enhanced risk of injuring the anatomical parts of the body such as the tissues, nerves etc. that are located near the target internal body part.

Therefore, a need exists in the art for an ultrasound probe with an integrated needle assembly and a computer program product, a method and a system for providing a path for inserting a needle of the ultrasound probe which does not suffer from above mentioned deficiencies.

SUMMARY OF THE INVENTION

In accordance with teachings of the present invention a device for providing a path for inserting a needle inside a body of a patient for performing medical procedures is provided.

An object of the present invention is to provide a device having an ultrasound probe housing, a guide channel cut-out or aperture, and a needle guide assembly. The ultrasound probe housing generates ultrasound waves to produce images inside of the body of a patient. The ultrasound probe housing has an ambient side and a body side and can be of any shape meeting the requirements of the invention. The ultrasound probe housing may also provide an adhesion or suction quality to the body side of the device to facilitate aspects of the invention.

The guide channel cut-out or aperture is configured between the ambient side and the body side through the ultrasound probe housing. The needle guide assembly may pivotally connect internal to the guide channel cut-out or aperture on the body side of the ultrasound probe housing at a pivot point. The needle guide assembly receives a needle. A needle is adapted to slide within the needle guide assembly such that during use the needle enters the patient through the needle guide assembly within the ultrasound probe housing so that the needle can be visualized by the ultrasonic probes in real time.

Another object of the invention is to provide a device with a rotation angle sensor. The rotation angle sensor is configured at or near the pivot point and connected with the needle guide assembly or sufficiently close to the needle guide assembly to approximate the needle angle within the assembly. Further, the rotation angle sensor can be a potentiometer.

Another object of the invention is to provide a device with a rotation angle sensor. The rotation angle sensor is configured at or near the pivot point and connected with the needle guide assembly or sufficiently close to the needle guide assembly to approximate the needle angle within the assembly. Further, the rotation angle sensor can be a potentiometer.

Another object of the invention is to provide a device with a locking mechanism that will hold the angular position of the needle to a fixed position as selected by the operator as to hold the needle in a fixed angular position while the procedure is being conducted.

Another object of the invention is to provide a device with an angle of rotation of the needle guide assembly inside the guide channel cut-out or aperture of the ultrasound probe housing. The guide channel cut-out or aperture may be a slot within the ultrasound probe housing giving an angle of rotation within a range of 0 degrees to roughly 180 degrees, or may be a more complex shape, such as conical shape, to further increase the degree of rotation of the needle guide assembly beyond that of a slotted shape. Further, the needle guide assembly is configured to be actuated by either mechanical unit or electrical unit. A person skilled in the art may appreciate that range of motion of the needle guide assembly may be assisted by the use of movement aids such as a bearing collar.

Another object of the invention is to provide the device with a pressure transducer is configured to be disposed in the needle.

Another object of the invention is to provide a path for inserting a needle into a body of a patient for performing medical procedures involving an ultrasound probe. The method includes steps of receiving images of inside of body of a patient generated corresponding to reflected ultrasonic waves, from an ultrasound probe housing, generating real-time 3-Dimensional (3D) images of anatomical parts of the body between the ultrasound probe and a target internal body part, displaying the real-time 3D images on a display device connected with the ultrasound probe, optionally comparing the real-time 3D images with pre-stored reference data stored in a data repository, and providing a path for inserting the needle through the ultrasound probe towards the target internal body part. A path or paths may be displayed as a visual overlay on the display device displaying the underlying anatomy, and may be generated with the assistance of computer software, for example with the use of artificial intelligence. The path or paths may be based on the available information that is both general (non-patient specific) and/or patient specific. The operator may then accept a path in space within the patient or choose a different path. The system receiving, processing, and providing an output may be a desktop PC, notebook, handheld, or mobile device, such as a smartphone, being linked in a wired or wireless form to the ultrasound probe.

Another object of the invention is to provide the step of guiding the needle on the provided path to the target internal body part through an automated and rotatable needle guide assembly, wherein the needle being covered in the field of view of the ultrasound probe is displayed on the display device during insertion.

Another object of the invention is to provide the step of guiding the needle on the provided path to the target internal body part using a needle insertion handle provided on the needle through the rotatable needle guide assembly, wherein the needle being covered in the field of view of the ultrasound probe is displayed on a display device during insertion, and wherein the needle insertion handle provides enhanced maneuverability for the practitioner/user.

Another object of the present invention is to provide the step of providing one or more of 3D images of the previously performed medical procedures, previously provided paths for similar procedures and images and details of anatomical parts of the body. Such images may be specific to the patient having the procedure performed with the device or method of the invention, and may be general in nature.

An object of the present invention is to provide a device having an ultrasound probe housing. The ultrasound probe housing generates ultrasound waves to produce images inside of the body of a patient. The ultrasound probe housing has an ambient side and a body side. The ultrasound probe housing provides an adhesion or suction quality to the body side of the device.

Another object of the device is to allow the ultrasound array and other various device components to be removed, maintained, or replaced for sterility, cleaning and other maintenance functions.

BRIEF DESCRIPTION OF THE DRAWINGS

So that the manner in which the above recited features of the present invention can be understood in detail, a more particular description of the invention, briefly summarized above, may have been referred by examples, some of which are illustrated in the appended drawings. It is to be noted, however, that the appended drawings illustrate only typical examples of this invention and are therefore not to be considered limiting of its scope, for the invention may admit to other equally effective examples.

These and other features, benefits, and advantages of the present invention will become apparent by reference to the following text figure, with like reference numbers referring to like structures across the views, wherein.

DETAILED DESCRIPTION OF THE EMBODIMENTS

While various embodiments of the present disclosure are provided herein, it should be understood that they are presented as examples only, and are not intended to be limiting. Similarly, the drawings and diagrams depict structural or architectural examples or alternate configurations of the invention, which are provided to aid in understanding the features and functionality of the various embodiments of the invention but are not intended to be limiting. The embodiments and features may be implemented and/or altered in a variety of ways known to those of ordinary skill the art.

Figure 1:
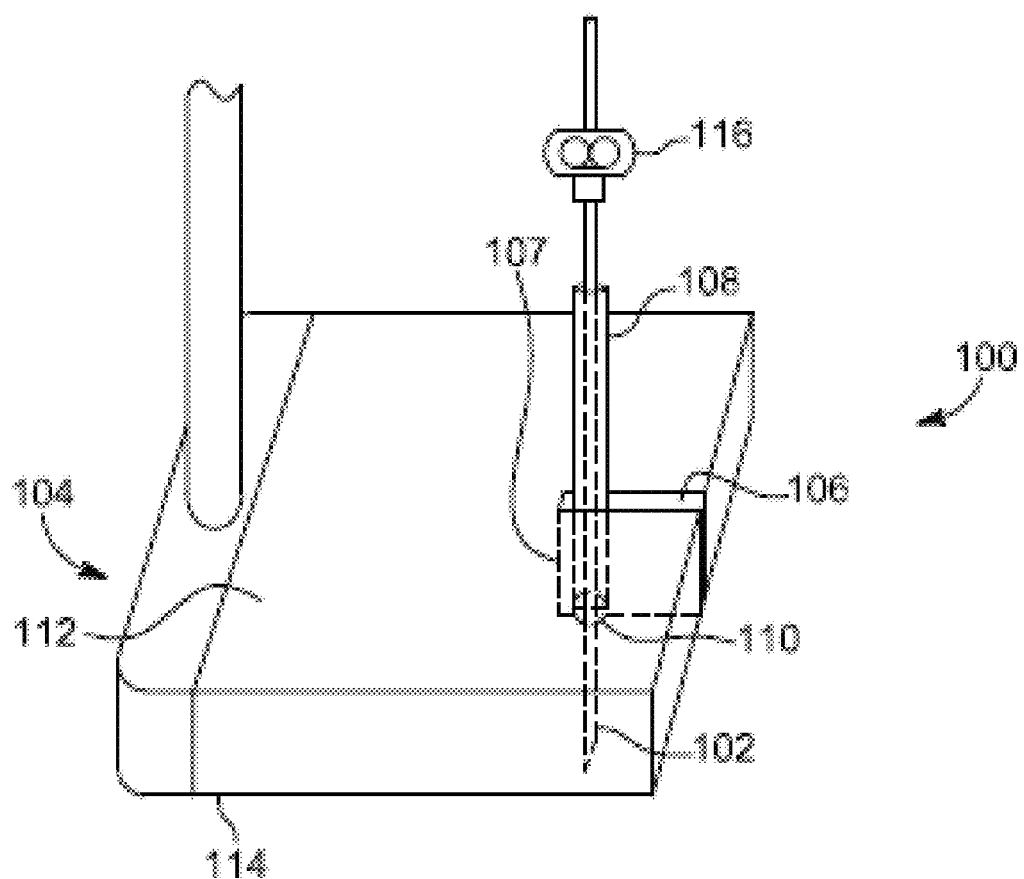
FIG. 1 illustrates a perspective view of a device providing a path for inserting a needle for performing medical procedures, in accordance with an embodiment of the present invention.

FIG. 1 illustrates a perspective view of a device 100 providing a path for inserting a needle 102 for performing medical procedures, in accordance with an embodiment of the present invention. The device 100 includes an ultrasound probe housing 104, a guide channel cut-out or aperture 106, and a needle guide assembly 108. In another embodiment of the present invention, the device 100 further includes a pivot point 110 and rotation angle sensor 111.

The ultrasound probe housing 104 contains a series of probes 105 (not shown) that generate ultrasound waves to produce images of inside of body of a patient. Ultrasound probe housing 104 having an ambient side 112 and a body side 114. Ultrasound probe housing 104 is explained in detail throughout and, for example, in conjunction with FIG. 3 of the present invention.

Guide channel cut-out or aperture 106 is configured between the ambient side 112 and the body side 114 through ultrasound probe housing 104. A needle guide assembly 108 pivotally connects to the guide channel cut-out or aperture 106 on the body side 114 of the ultrasound probe housing 104 at pivot point 110. The needle guide assembly 108 receives a needle 102. Needle 102 is adapted to slide in needle guide assembly 108 such that needle 102 enters the field of view of the ultrasound probe housing 104 upon insertion into the tissue of the patient receiving the procedure.

In an embodiment of the present invention, pivot point 110 is located near to left side 107 of the guide channel cut-out or aperture 106. However, it would be readily apparent to those skilled in the art to move pivot point 110 in the guide channel cut-out or aperture 106 to increase angle of rotation of needle 102 without deviating from the scope of the present invention.

Needle guide assembly 108 pivotally moves inside the guide channel cut-out or aperture 106 between a vertical setting and a shallow setting. As shown in FIG. 1, needle guide assembly 108 is at vertical setting. However, it would be readily apparent to those skilled in the art that the guide channel cut-out 106 may be created in multiple shapes such as circular, conical, hyperboloid, etc. to increase the angle of rotation to a desired angle without deviating from the scope of the present invention. The angle of rotation of the needle guide assembly 108 is explained by way of example in detail in conjunction with FIGS. 8 and 9 of the present invention.

Further in another embodiment of the present invention, the rotational angle sensor 111 is configured at pivot point 110 and connected with needle guide assembly 108 to measure needle location. The rotational angle sensor 111 is a potentiometer. In another embodiment of the present invention, the angle of rotation of the needle guide assembly 108 inside the guide channel cut-out or aperture 106 is in the range of 0 to 180 degrees.

In another embodiment of the present invention, device 100 further includes a needle insertion handle 116 for allowing practitioner/user 706 to hold and move needle 102 inside needle guide assembly 108. Needle guide assembly 108 is a rigid housing that is manually or automatically adjusted and provides a predetermined and rigid path to allow for precise needle insertion to the target. Needle insertion handle 116 may be a conventional cuboid plastic grip but can be modified for improved control and tactile response required in a procedure. Needle insertion handle 116 may include a plastic (or suitable material) shape such as a wing tip, protrusion, or fingerhold that resides at a distance away from the end of the needle to allow for more control with needle insertion, as shown in FIG. 1. Modifying needle insertion handle 116 may obviate practitioner/user 706 need or desire to handle needle 102 directly during the procedure. Further, needle guide assembly 108 will stabilize needle 102 in the x axis to improve practitioner/user 706 needle usage.

Figure 2:
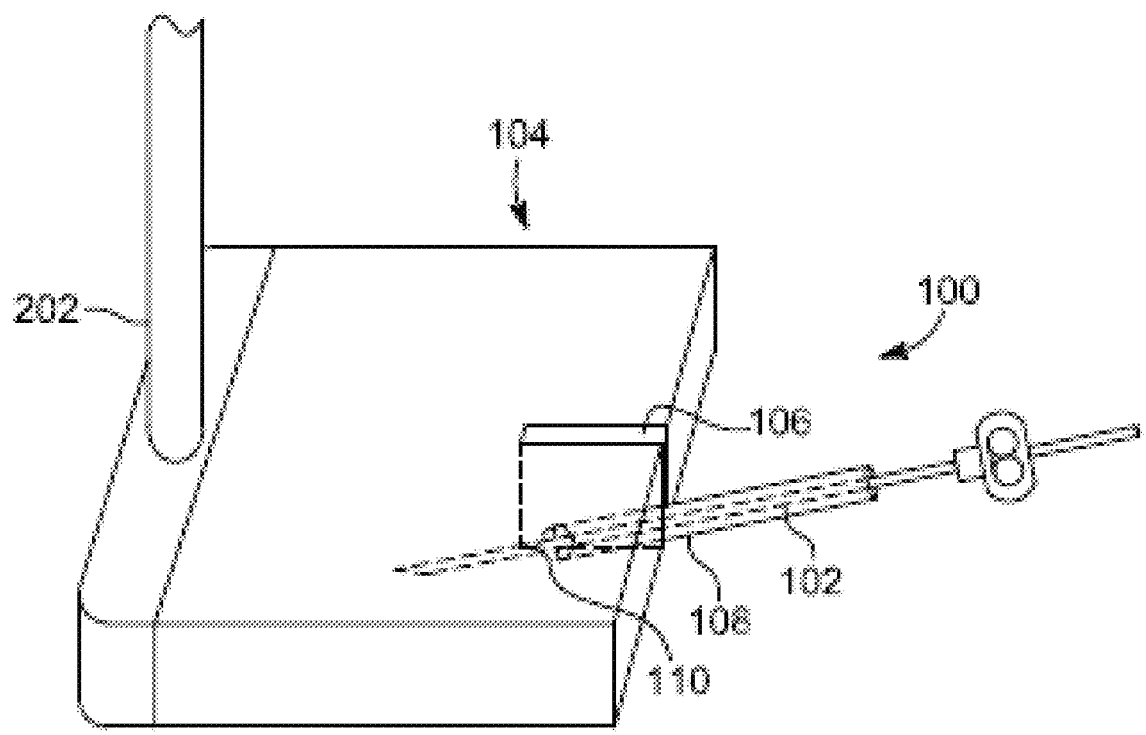
FIG. 2 illustrates another perspective view of a device providing a path for inserting a needle for performing a medical procedure, in accordance with another embodiment of the present invention.

FIG. 2 illustrates another perspective view of the device 100 providing a path for inserting needle 102 for performing medical procedure, in accordance with another embodiment of the present invention. Needle guide assembly 108 is at the shallow setting.

Needle guide assembly 108 is movable by practitioner/user 706 within guide channel cut-out or aperture 106 at any desired angle. Alternatively, needle guide assembly 108 is actuated either by a mechanical unit (such as levers) or an electrical unit (such as robotic arm). In another embodiment of the present invention, device 100 may further include a cord 202 to supply power and transmit data to ultrasound probe housing 104.

In another embodiment of the present invention, guide channel cut-out or aperture 106 is a U shape cut at the edge of the ultrasound probe housing 104. However, it would be readily apparent to those skilled in the art that various shapes (such as V-shaped) and place (such as center) to create the guide channel cut-out or aperture 106 on the ultrasound probe housing 104 may be envisioned without deviating from the scope of the present invention.

Figure 3A:
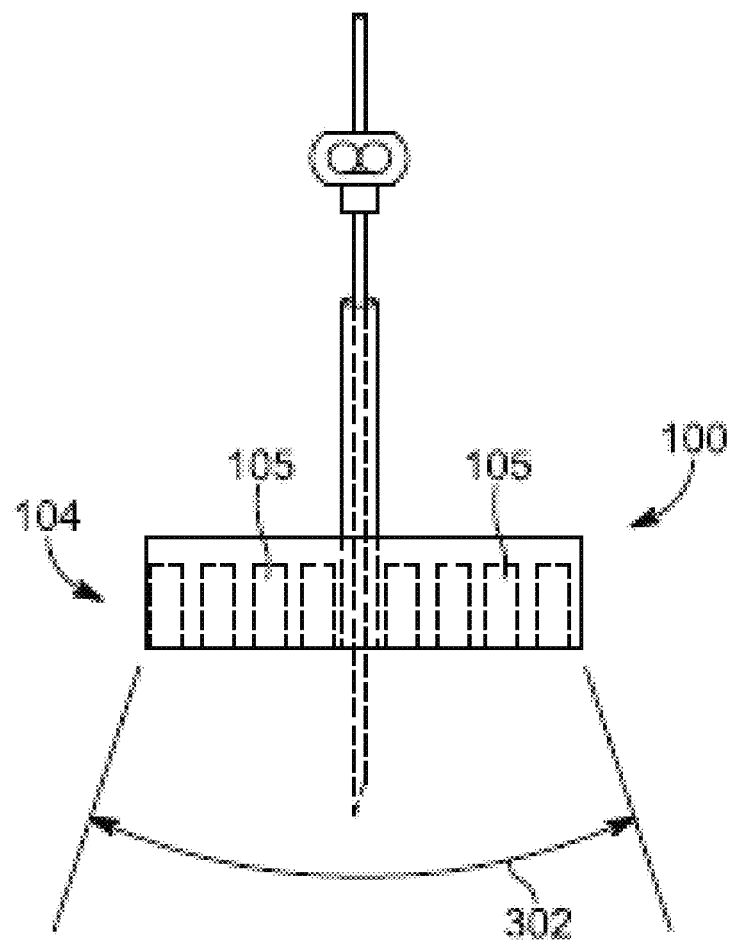
FIG. 3A illustrates a front view of a device in accordance with an embodiment of the present invention.
Figure 3B:
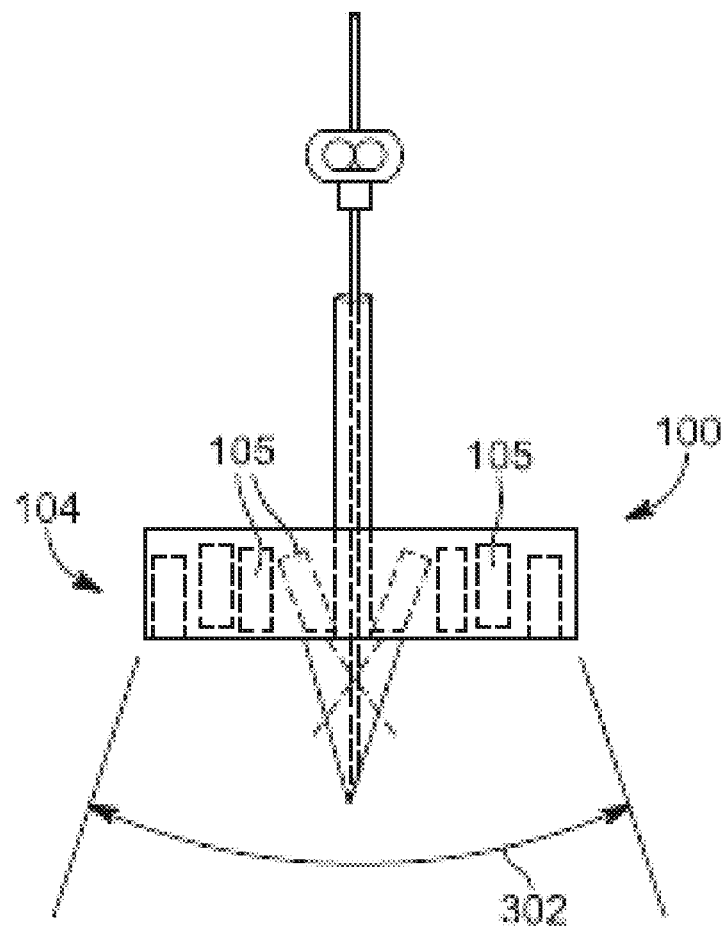
FIG. 3B illustrates a front view of a device in accordance with another embodiment of the present invention.

FIG. 3A illustrates a partial front view of device 100 in accordance with an embodiment of the present invention. Ultrasound probe housing 104 contains probes 105 that generate ultrasonic waves, receive the reflected ultrasonic waves and generate data in the form of electrical signals corresponding to the received ultrasonic waves.

Ultrasound probe housing 104 generates real-time 3-Dimensional (3D) images of anatomical parts of the body of the patient. A field 302 shows the viewable image area beneath and near the ultrasound probe housing 104. As shown by example in FIG. 3B, the array of probes 105 may be positioned within ultrasound probe housing 104 to alter the viewable image of field 302. In certain formats, probes 105 may be angled within ultrasound probe housing 104 to optimize the viewable image at the site of needle penetration beneath ultrasound probe housing 104. This may be helpful to accommodate changes to the structure of guide channel cut-out or aperture 106. Likewise, probes 105 may be positioned perpendicular to body side 114 of ultrasound probe housing 104 to give a wider viewable image area. Ultrasound probe housing 104 may also contain a mixed array of angled and perpendicular probes 105 to alter viewable image geometries. It would be readily apparent to those skilled in the art that various types and shapes of ultrasound probe housing 104 containing probes 105 may be envisioned without deviating from the scope of the present invention.

Figure 4A:
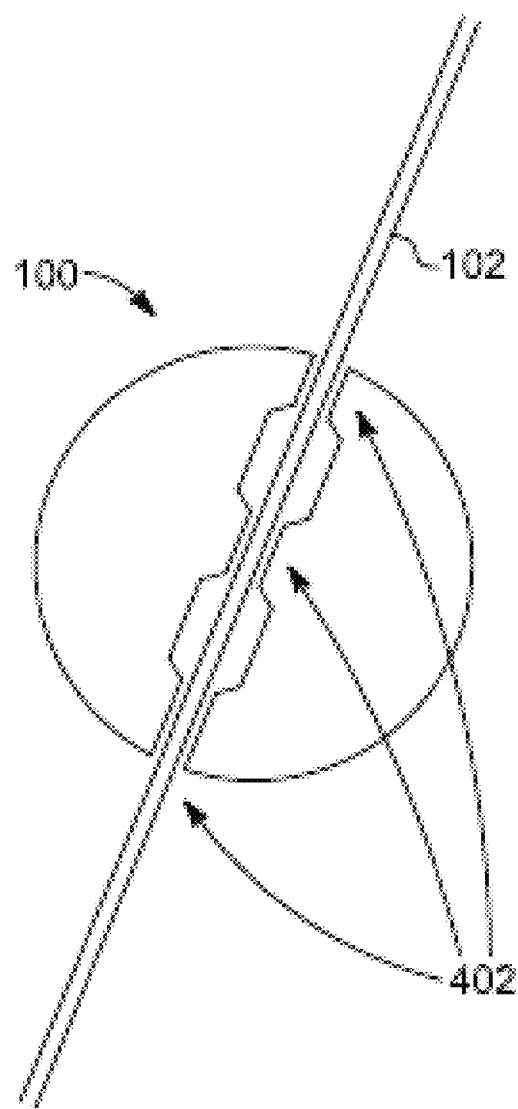
FIG. 4A illustrates a perspective view of a needle guide assembly in accordance with an embodiment of the present invention.

FIG. 4A illustrates a perspective view of needle 102 in accordance with an embodiment of the present invention. In another embodiment of the present invention, device 100 further includes plurality of guide bearings 402 to facilitate sliding motion of needle 102 in needle guide assembly 108 (as shown by example in FIG. 1 to FIG. 3). Needle guide assembly 108 stabilizes needle 102 during insertion into the patient body and attaches needle 102 to ultrasound probe housing 104.

Figure 4B:
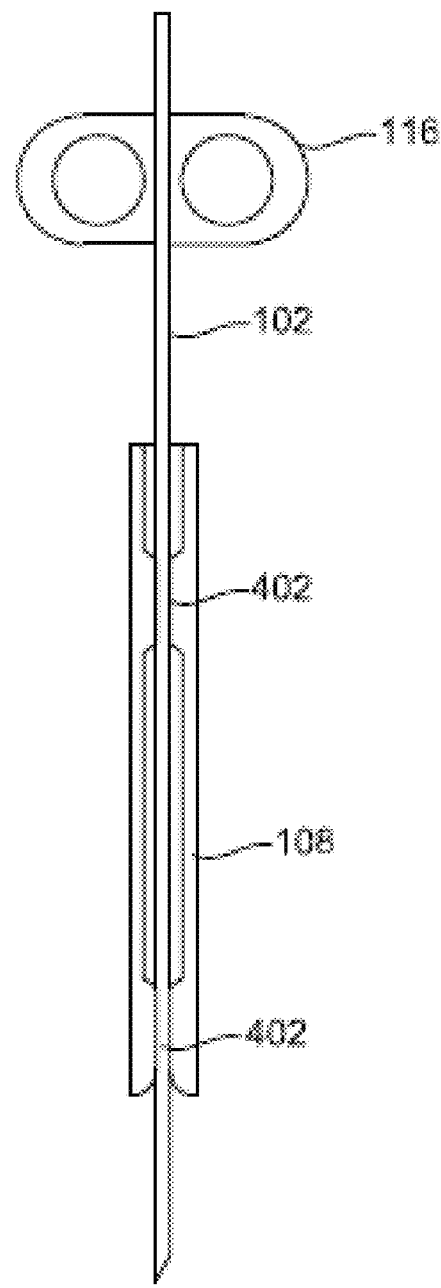
FIG. 4B provides another perspective view of needle in accordance with an embodiment of the invention.

FIG. 4B provides another perspective view of needle 102 in accordance with an embodiment of the invention. FIG. 4A further includes exemplary needle insertion handle 116. It will be appreciated that examples of guide bearings 402 include but are not limited to 1 or more sliding bearings designed to allow needle 102 to move in the radial direction, restricts the needle from bending on insertion, and maintains the needle position in space.

Figure 5:
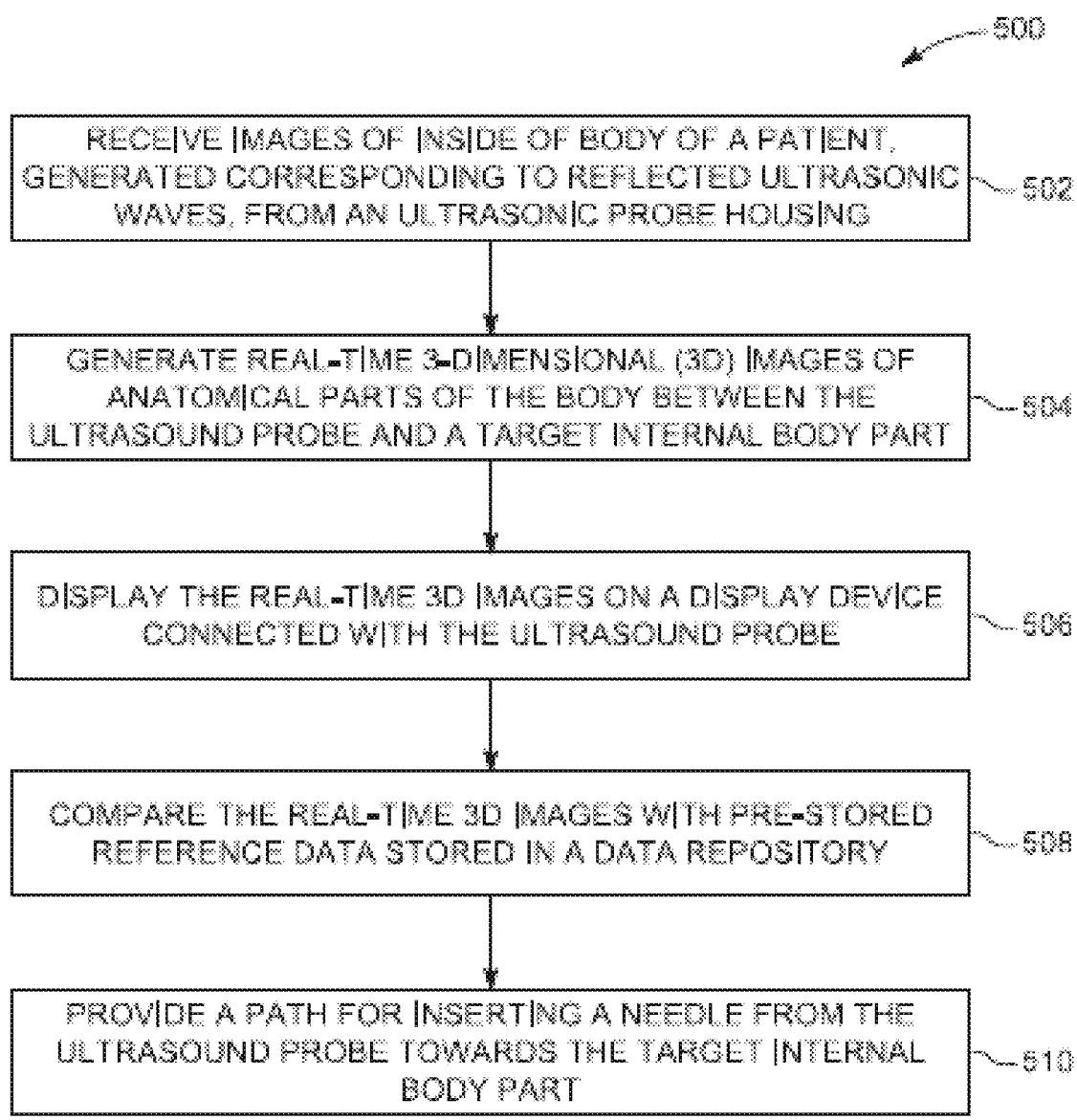
FIG. 5 illustrates a method for providing a path for inserting a needle of the ultrasound probe inside a body of a patient, in accordance with an embodiment of the present invention.

FIG. 5 illustrates a method 500 for providing a path for inserting inside a body of a patient during medical procedures involving an ultrasound probe housing in accordance with an embodiment of the present invention. The method 500 initiates with a step 502 of receiving images of inside of body of a patient, generated corresponding to reflected ultrasonic waves from probes 105 of ultrasound probe housing 104. Ultrasound probe housing 104 of step 502 is explained in detail in conjunction with FIG. 1 and FIG. 3 of the present invention.

Step 502 is followed by a step 504 of generating real-time 3-Dimensional (3D) images of anatomical parts of the body between the ultrasound probe and an internal target body location. Data from ultrasound probe housing 104 is transmitted to a processor. The processor processes received data and generates 3D images of anatomical parts in real-time.

Step 504 is followed by a step 506 of displaying the real-time 3D images on a display device receiving information from device 100. The processor processes the data received from the ultrasound probes and the display device displays the processed data. The display device may also display a predicted path 705 of needle 102 based on the current body location of device 100 and current needle angular position. Predicted path 705 represents the path that needle 102 would take through the patient anatomy if needle were extended in space from and based on its current coordinates. The display device and the processor is explained herein and also in further conjunction with FIG. 6 of the present invention.

Figure 6:
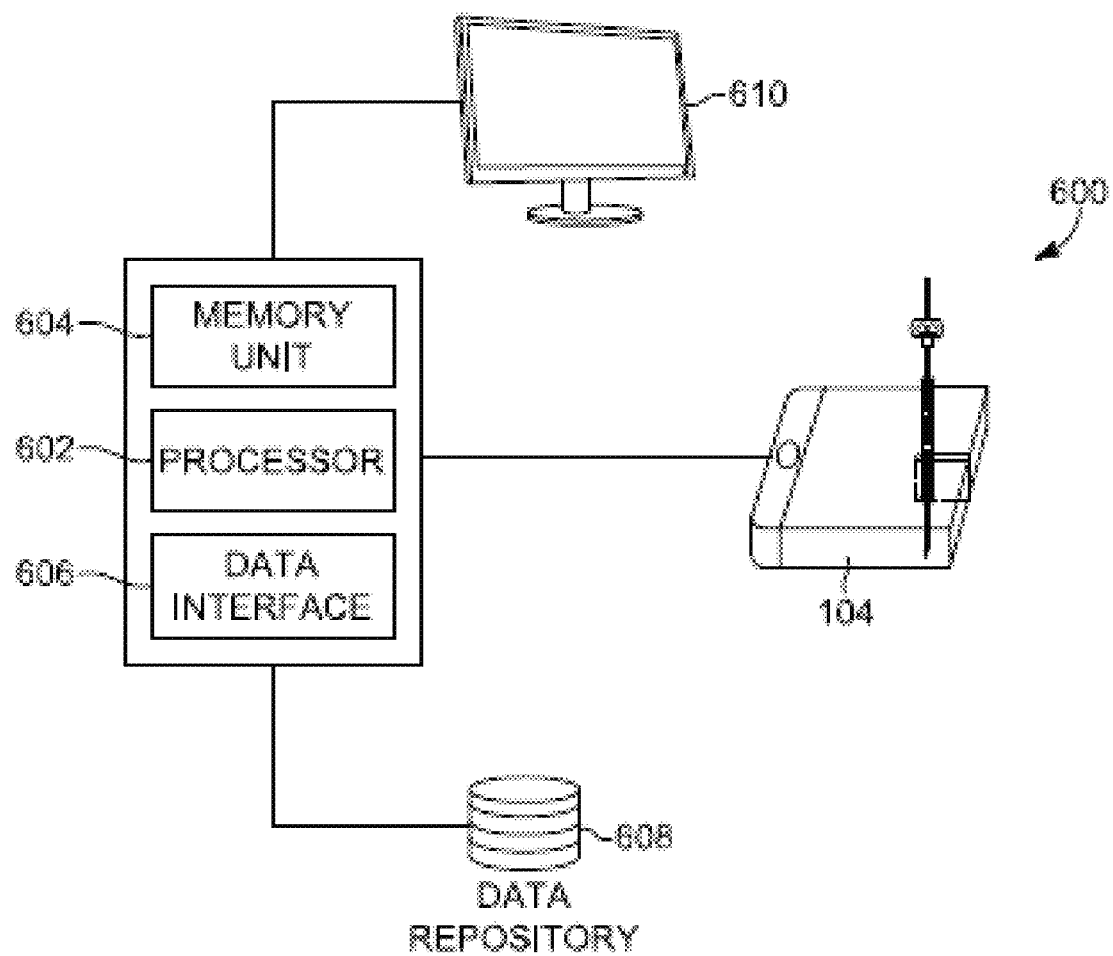
FIG. 6 illustrates a system for providing a path for inserting a needle for medical procedures, in accordance with an embodiment of the present invention.

Step 506 may optionally be followed by a step 508 of comparing the real time 3D images and data with reference data stored in a data repository 608 (as shown by example in FIG. 6). Data repository 608 may also be at a remote location but accessible in real time, such as with cloud storage. Further, step 506 or 508 may then be followed by step 510 of providing a recommended path 707 for inserting needle 102 through the ultrasound probe housing towards the internal target body location. Recommended path 707 is a path through the anatomy of the patient based on available data that may include current real time data from device 100, stored data, and the type of procedure to be performed. The recommended path 707 for inserting needle 102 through the ultrasound probe is displayed on the display device. Both the distance and angle of the device from its current position to the position matching that of the recommended path can be displayed to enable practitioner/user 706 to relocate the device on the patient body to be able to match the recommended path. Predicted path 705 and recommended path 707 may differ from each other. Practitioner/user 706 has the option to use the recommended path 707 or to select an alternate path based on the real time 3D image display and predicted path 705.

Examples of the pre-stored data include but not limited to one or more 2D and 3D images of the previously performed medical procedures that can be patient-specific, previously provided paths for similar procedures, and images and details of anatomical parts of the body, etc.

In an exemplary embodiment of the present invention, the 3D image shows a kidney of a patient in real time, then the processor compares the real time 3D image with the pre-stored data. The pre-stored data showcase the path for inserting needle 102 that corresponds to the image of the kidney. The desired path to perform the medical procedure is displayed on the display device depending upon the real time image.

It would be readily apparent to those skilled in the art that artificial intelligence may be involved at various stages of information usage for the device. For example, AI may assess the path of treating the internal target body location from the data repository 608 (shown in FIG. 6) and may identify a recommended path 707 (shown in FIG. 7) on receiving the similar situation without deviating from the scope of the present invention.

FIG. 6 illustrates a system 600 for providing a path or paths for inserting needle 102 for medical procedures, in accordance with an embodiment of the present invention. The system 600 further includes an ultrasound probe housing 104, a guide channel cut-out or aperture 106, needle guide assembly 108, a processor 602, a memory unit 604, a data interface 606, a data repository 608 and a display unit 610.

The ultrasound probe housing 104, the guide channel cut-out or aperture 106 and needle guide assembly 108 are explained in detail in conjunction with exemplary FIG. 1 to FIG. 3 of the present invention. Processor 602 is connected with the ultrasound probe housing 104 through the data interface 606, which may or may not be a physical, wired connection. For instance, data interface 606 may receive data from a wireless, cellular, or bluetooth connection. Thus, processor 602 may be connected to ultrasound probe housing via a wired or wireless connection.

The data interface 606 receives data from the ultrasound probe housing 104 and transfers the received data to the processor 602 for processing. Examples of the processor 602 can include any system that processes images to predict and map the real patient's anatomy during the live procedure based on changes in echogenecity during the ultrasound. This can include the use of AI or other simulated intelligent programs.

The memory unit 604, the display unit 610 and the data repository 608 are connected with the processor 602, and may each be stand-alone equipment or could be a composite device, such as a desktop PC, notebook, handheld, or mobile device, such as a smartphone. The memory unit 604 stores the instructions, the processor 602 processes the stored instructions and the display unit 610 displays the processed instructions. The instructions are explained in the conjunction with FIG. 5 (method 500) of the present invention.

Examples of the memory unit 604 include but not limited to a fixed memory unit or a portable memory unit that can be inserted into the device. It will be appreciated that memory unit 604 would have sufficient memory to adequately store large volumes of information. It is expected that each system may offer advantages in certain use situations. For example, a portable memory unit may also be insertable into and compatible with an available medical record system for information exchange. A fixed memory unit may achieve a similar goal by having a port for information exchange. Examples of the display unit 610 include but not limited to LCD, LED, OLED, TFT, or any specific display of any unit device capable of visually providing information such as on a desktop PC, notebook, handheld, or mobile device, such as a smartphone.

Figure 7:
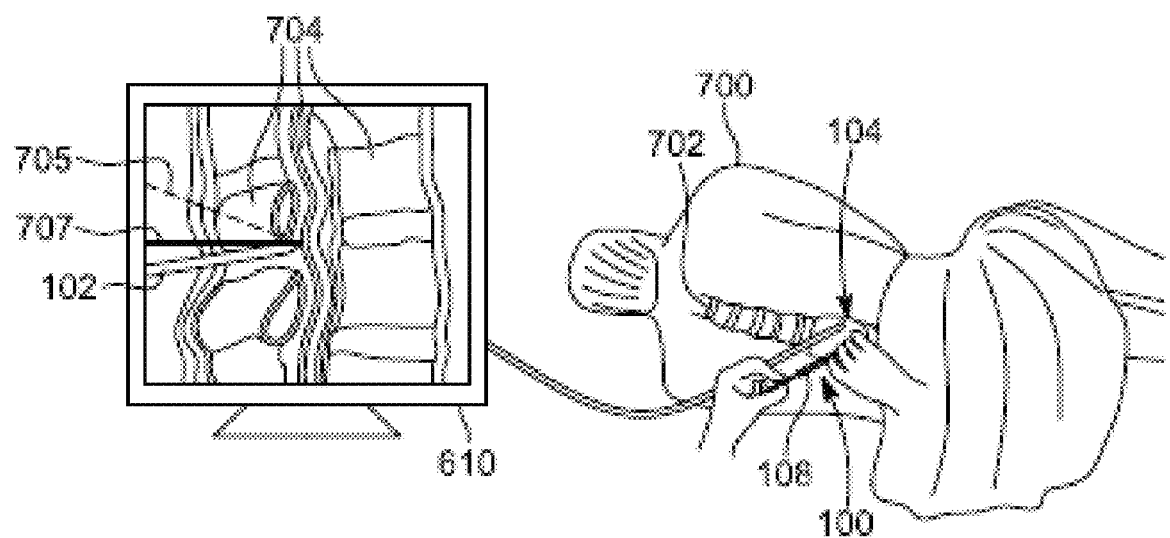
FIG. 7 illustrates a schematic diagram of performing medical procedures on the patient using a device in which a pathway for needle insertion into the patient is provided, in accordance with an embodiment of the present invention.

FIG. 7 illustrates a schematic diagram of performing medical procedure on the patient 700 using the device 100, in accordance with an embodiment of the present invention. In this example, ultrasound probe housing 104 is placed on the back of the patient 700 to perform a medical procedure on spine 702.

The ultrasound probe housing 104 captures images of spine 702 and other anatomical body parts 704 of patient 700 and displays the images on the display device 610 in real time. The display of spine 702 and anatomical body parts 704 allows a practitioner/user 706 to move needle 102, which is placed inside needle guide assembly 108, through the guide channel cut-out or aperture 106 to perform the required medical procedure on the desired location of the body part of the patient 700.

Device 100 allows practitioner/user 706 to perform the medical procedure with greater ease and on the desired location. Due to its location within and through ultrasound probe housing 104, the visibility of needle 102 in 3D allows practitioner/user 706 viewing of the desired location from multiple angles for improved procedural accuracy.

Further, FIG. 7 illustrates use of device 100 where the pathway for insertion of needle 102 through ultrasound probe housing 104 is predicted and displayed on display unit 610 based on information collected in real time and/or from data repository 608 of system 600. The control unit will take the angular position input from the potentiometer and automatically adjust the optimum angle of needle 102 via a motor to pass between anatomical structures, for example, spinous processes, for procedural success. The angle of needle 102 may also be manually managed by a movement mechanism such as a turning dial to set a final needle path. Practitioner/user 706 can choose to follow predicted path 705 for needle 102, recommended path 707 for needle 102, or some other path of the operator's choosing. Once practitioner/user 706 selects an insertion pathway, needle guide assembly 108 is locked in position to allow needle 102 to be inserted along the selected path. Depending on the embodiment of the device, practitioner/user 706 would also be able to stabilize the device location relative to the patient body by actuating attachment features of device 100 discussed herein. The insertion of needle 102 can be manually or automatically driven by or through device 100. It will be appreciated that system 600 will use computer processing in determining and displaying predicted path 705 and recommended path 707, and such processing may be based on artificial intelligence. In another embodiment of the invention, the display device may further display anticipated procedural steps to be performed for the specific procedure being undertaken by practitioner/user 706. Upcoming procedure steps may be indicated as textual prompts, bubble callouts, audibles, and may also include voice commands or prompts.

Figure 8A:
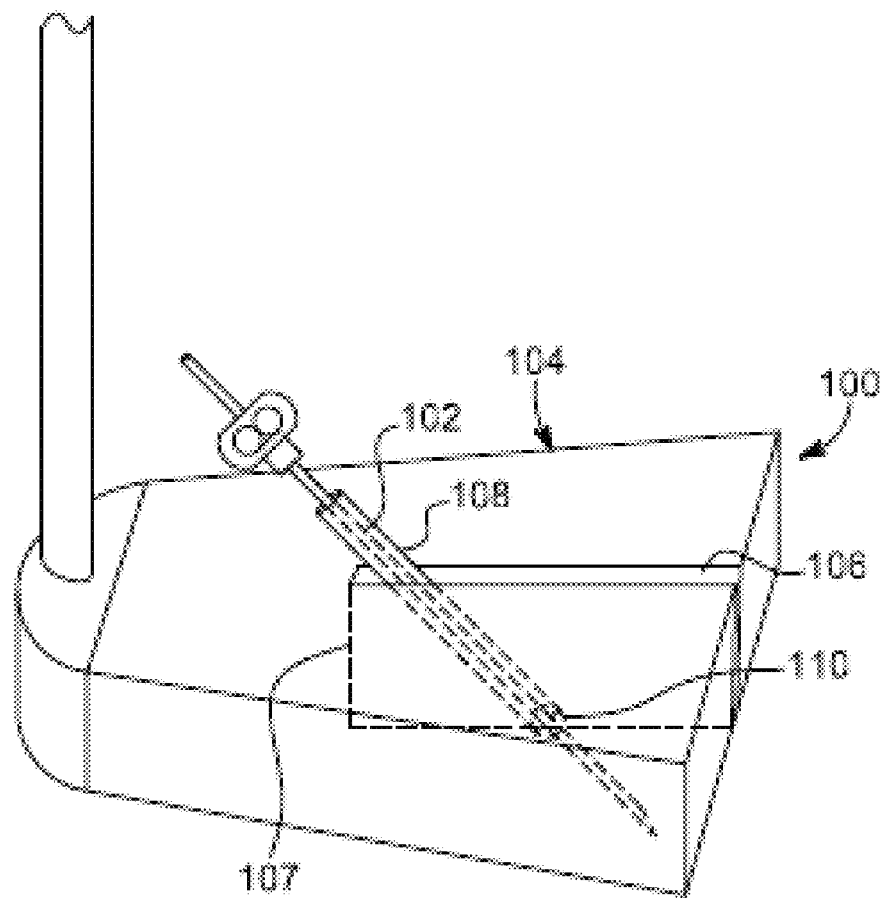
FIG. 8A illustrates a perspective view of the device providing a path for inserting a needle for performing a medical procedure, in accordance with an embodiment of the present invention.
Figure 8B:
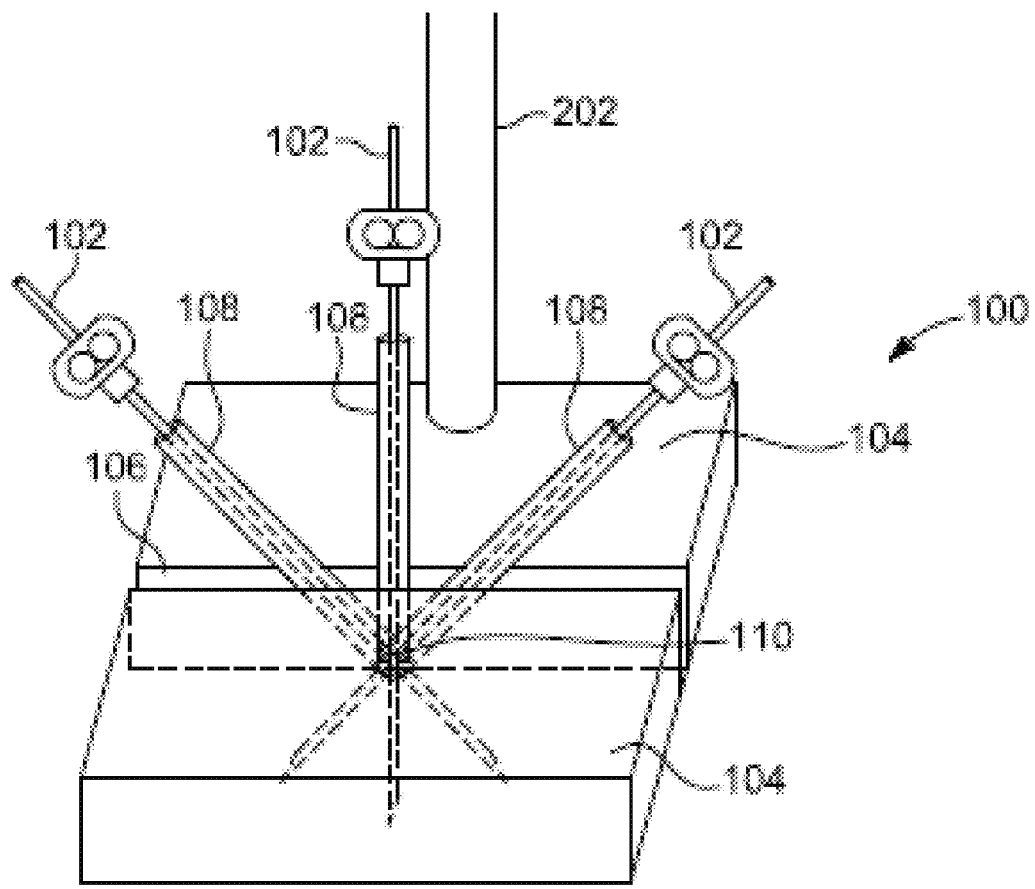
FIG. 8B illustrates a perspective view of the device providing a path for inserting a needle for performing a medical procedure, in accordance with another embodiment of the present invention.
Figure 9A:
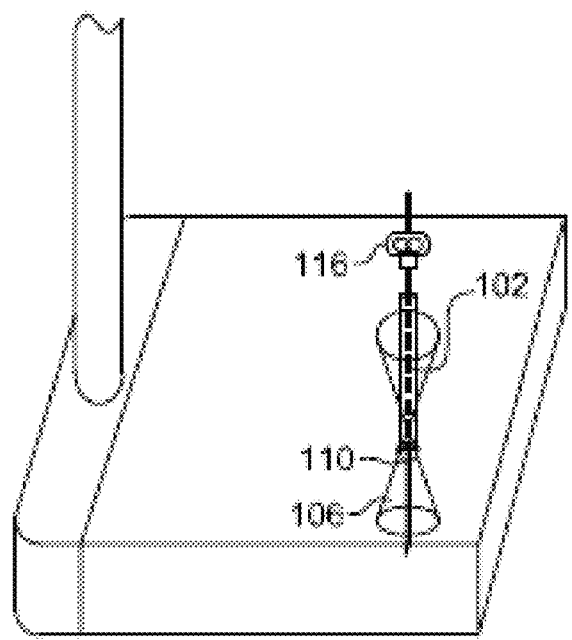
FIG. 9A illustrates a perspective view of the device providing a path for inserting a needle for performing medical procedure, in accordance with another embodiment of the present invention.
Figure 9B:
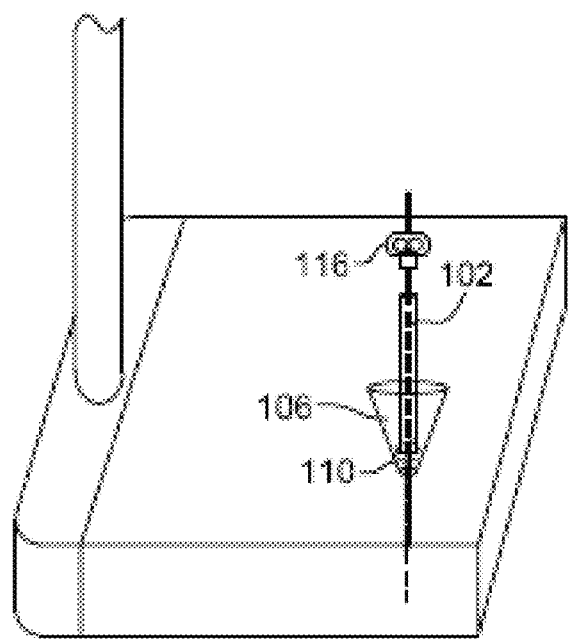
FIG. 9B illustrates a perspective view of the device providing a path for inserting a needle for performing medical procedure, in accordance with another embodiment of the present invention.
Figure 9C:
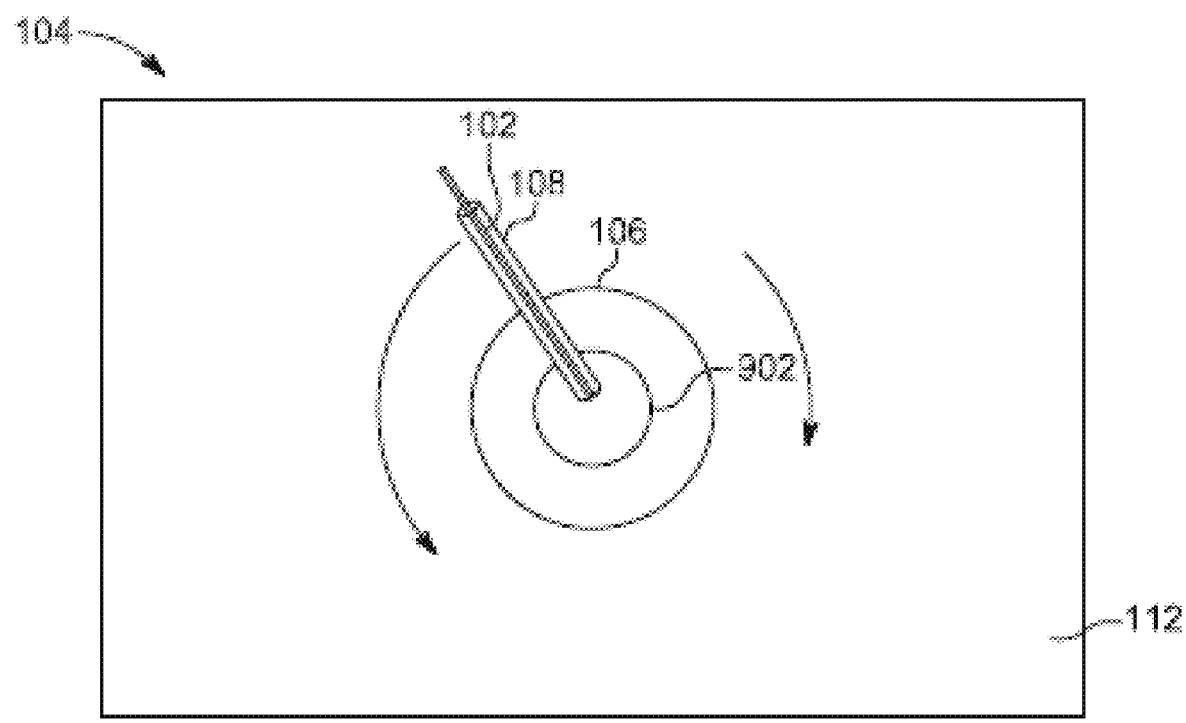
FIG. 9C illustrates a top view of the device providing a path for inserting a needle for performing medical procedure, in accordance with another embodiment of the present invention.
Figure 9D:
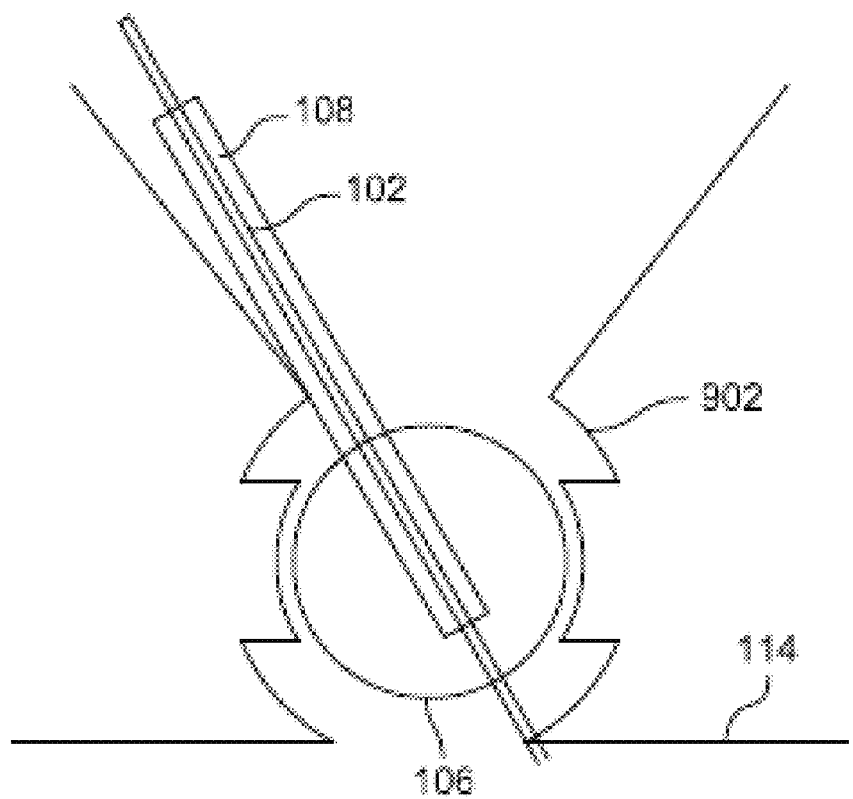
FIG. 9D illustrates a side view cutaway of the device providing a path for inserting a needle for performing medical procedure, in accordance with another embodiment of the present invention.

FIG. 8A illustrates another perspective view of the device 100 providing a path for inserting a needle 102 for performing the medical procedure, in accordance with another embodiment of the present invention. The length of the guide channel cut-out or aperture 106 is extended to allow needle guide assembly 108 to rotate in both directions within the channel-like structure, i.e., up to 180 degrees of total range of movement. Pivot point 110 is now away from the left side 107 of the guide channel cut-out or aperture 106. The needle guide assembly 108 passes through pivot point 110 and thus the angle of rotation increases from approximately 0 to 90 degrees to a fuller range of 0 to 90 degrees and 0 to minus 90 degrees. FIG. 8B provides another example where guide channel cut-out or aperture 106 provides a greater range of motion over device 100 as depicted in exemplary FIG. 1. In this embodiment, it will be appreciated that guide channel cut-out or aperture 106 has rotated from the direction provided in FIG. 8A. It will further be appreciated that the location of guide channel cut-out or aperture 106 is not fixed so long as needle 102 exits through body side 114 of ultrasound probe housing 104 of device 100 to achieve the purposes of the invention.

FIG. 9 illustrates various views of device 100 for providing a path for inserting needle 102 for performing a medical procedure with guide channel cut-out or aperture 106 having cone-like geometries. Needle guide assembly 108 pivotally connects to the guide channel cut-out or aperture 106 on or near the body side 114 of the ultrasound probe housing 104 at pivot point 110. In these configurations, needle guide assembly 108 and guide channel cut-out or aperture 106 may use a spherical bearing or similar device that allows needle 102 to rotate both radially and circumferentially, as shown in FIGS. 9C and 9D. Needle 102 is adapted to slide in needle guide assembly 108 such that the needle 102 is in a field of view of the ultrasound probe housing 104 upon insertion into the tissue of the patient receiving the procedure. It will be appreciated that guide channel cut-out or aperture 106 may be a cone or hyperboloid shape, for example as shown as in FIGS. 9A and 9B, to potentially provide greater degrees of movement over the guide channel cut-out or aperture 106 as depicture in FIG. 1. It would be readily apparent to those skilled in the art that various shapes and sizes of guide channel cut-out or aperture 106 may be envisioned without deviating from the scope of the present invention.

Figure 10A:
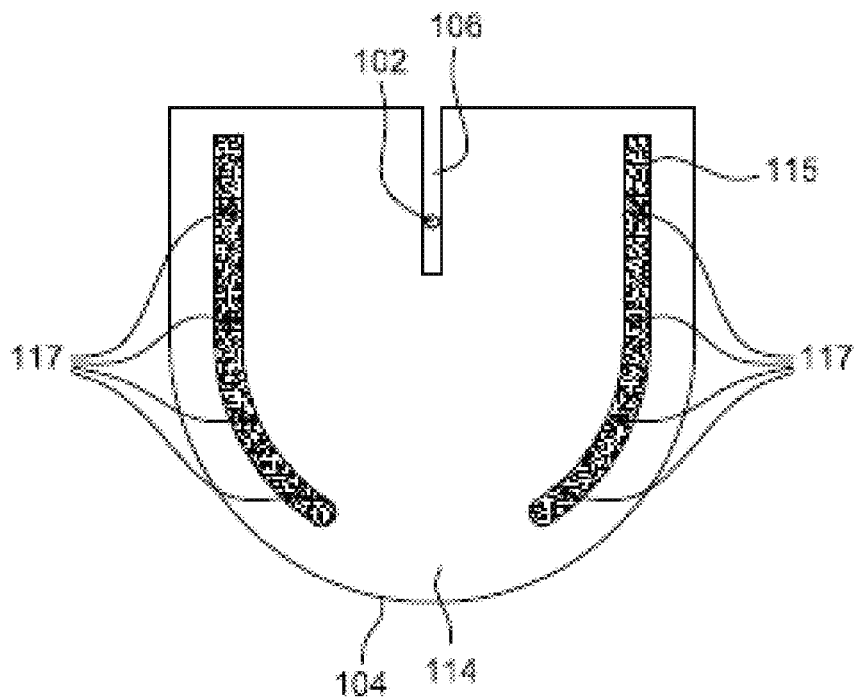
FIG. 10A illustrates a bottom view of the ultrasound probe housing having adhesion points located at the perimeter of the body side of the device in accordance with another embodiment of the present invention.

FIG. 10A illustrates a bottom view of ultrasound probe housing 104 of device 100 having adhesion points 115 located on body side 114 of ultrasound probe housing 104. Adhesion points 115, which may further contain holes 117, fix or adhere ultrasound probe housing 104 in location on the patient to maintain further control of the device for needle penetration. FIG. 10A depicts adhesion points 115 along the perimeter of ultrasound probe housing 104, but it will be appreciated that adhesion points 115 may be located anywhere across body side 114 of ultrasound probe housing 104 so long as they do not interfere with the ability of probes 105 to generate the viewable image field required for the procedure to be performed. FIG. 10A provides adhesion points 115 in the shape of elongated depressions, but adhesion points 115 may be any shape, such as channels, cups, cups with lips or pronounced outer edges, or may have no additional contouring different from body side 114 of ultrasound probe housing 104. It will be appreciated that ultrasound probe housing 104 may be held in place during the procedure by applying suction or tactile adhesion. Holes 117 may provide suction forces to adhesion points 115 in one format and may be a source of skin adhesive to adhere ultrasound probe housing 104 in place in another format.

Figure 10B:
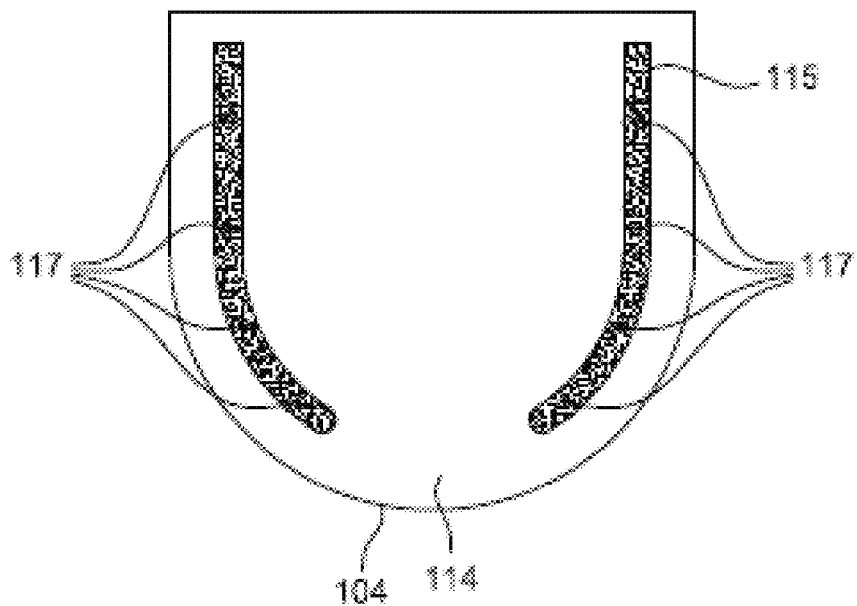
FIG. 10B illustrates a bottom view of the ultrasound probe housing having adhesion points located at the perimeter of the body side of the device in accordance with another embodiment of the present invention.

FIG. 10B provides a bottom of ultrasound probe housing 104 with no guide channel cut-out or aperture 106. This embodiment provides the fixing ability of ultrasound probe housing 104 as described herein with the ability to have needle 102 attached to the ultrasound probe housing 104 in an external manner, or to have needle 102 unattached completely per practitioner/user 706 preference. It will be appreciated that each of the devices disclosed having adhesion points 115 may be without guide channel cut-out or aperture 106 and still provide the ability to fix the device to the patient as desired.

Figure 11A:
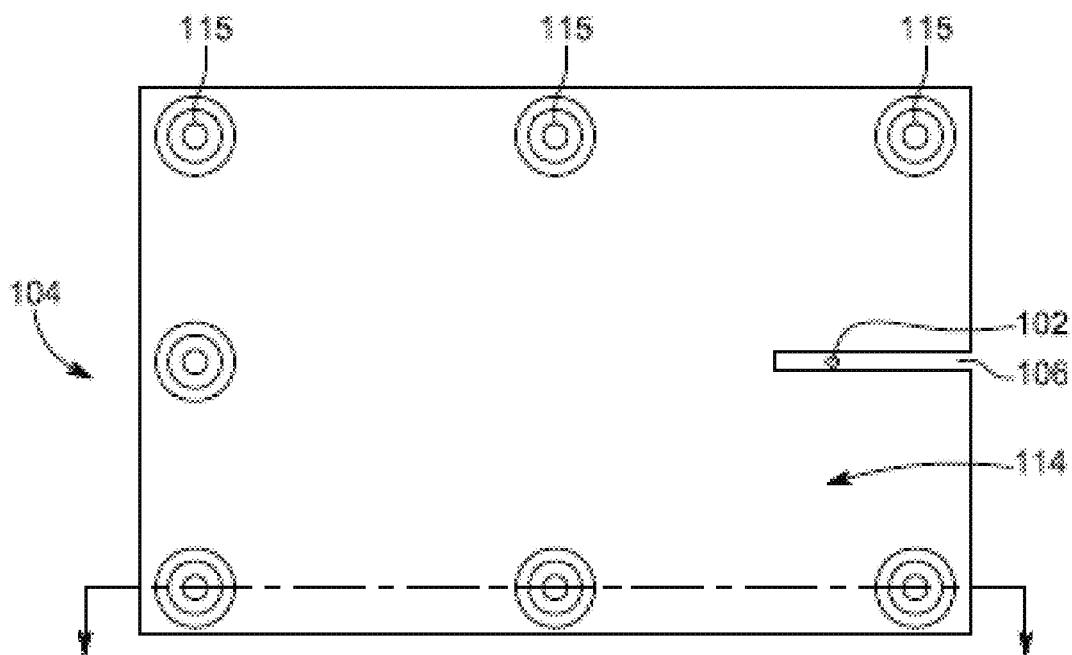
FIG. 11A illustrates a bottom view of the ultrasound probe housing having adhesion points located at the perimeter of the body side of the device in accordance with another embodiment of the present invention.
Figure 11B:
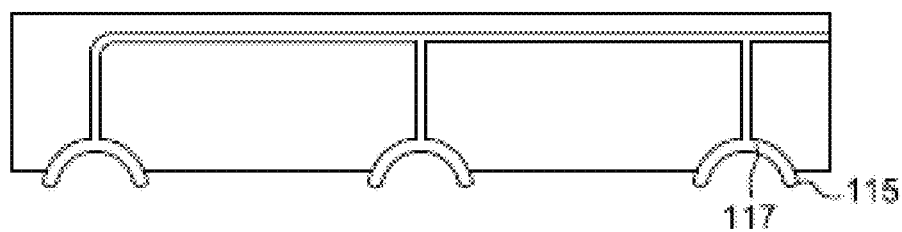
FIG. 11B provides a side cutaway view of the ultrasound probe housing having adhesion points located at the perimeter of the body side of the device in accordance with another embodiment of the present invention.

FIG. 11A demonstrates a bottom view of ultrasound probe housing 104 having adhesion points 115 located at the perimeter of the body side 114 of device 100 (shown in FIG. 1) in accordance with an embodiment of the present invention. FIG. 11B provides adhesion points 115 shaped as depressions with structure along the perimeter of said depressions to facilitate suction contact, e.g. suction cups. Adhesion points 115 further contain holes 117 through which suction forces may be applied to the contact point on the patient body. Ultrasound probe housing 104 contains internal structure such as tubing or channels for air exchange to create suction through holes 117. It will be appreciated that the exact architecture needed to facilitate suction forces can vary so long as it does not interfere with the purposes of this invention.

FIG. 11B provides a side cutaway view of ultrasound probe housing 104 in which adhesion points 115 and holes 117 are apparent and opened to body side 114. It will be appreciated that holes 117 and the corresponding architecture within ultrasound probe housing 104 may provide a source of adhesive instead of suction forces by which to fix device 100.

Figure 12A:
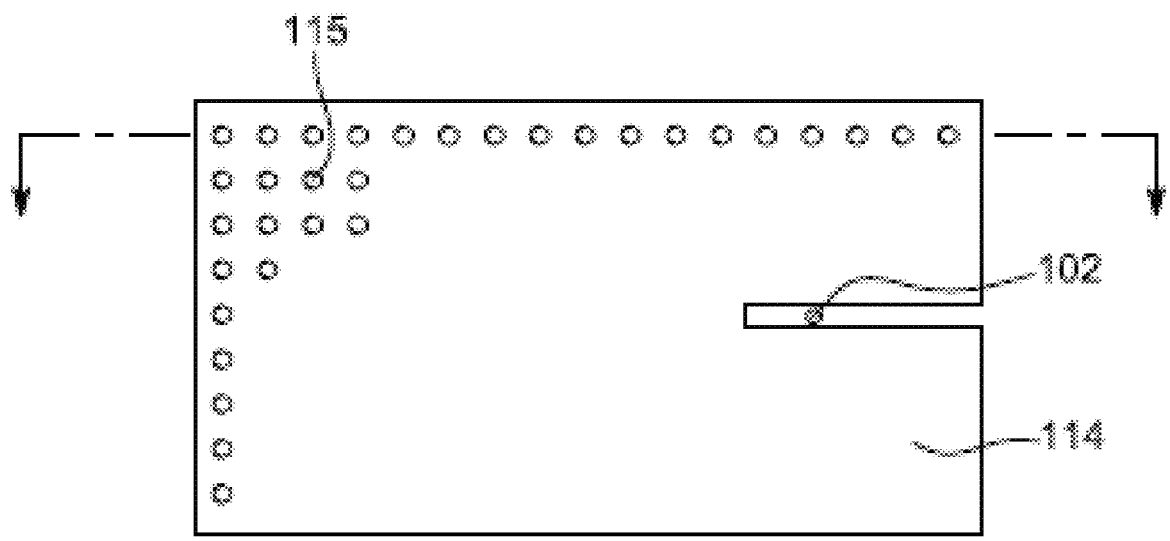
FIG. 12A illustrates a bottom view of the ultrasound probe housing having adhesion points located across the body side of the device in accordance with another embodiment of the present invention.
Figure 12B:
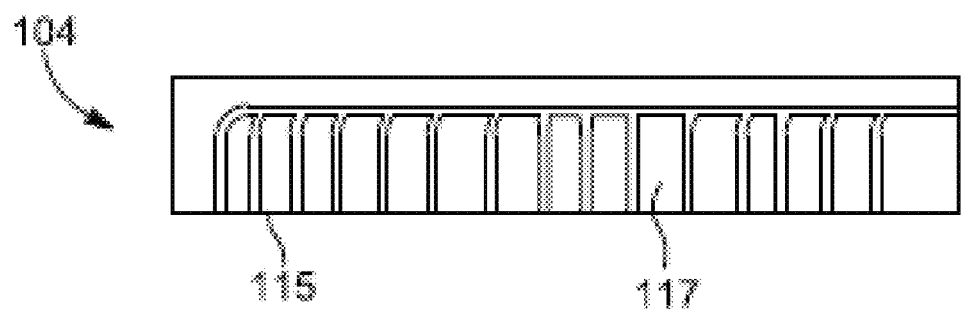
FIG. 12B illustrates a side cutaway view of ultrasound probe housing in which adhesion points and holes are apparent and opened to body side of the device in accordance with another embodiment of the present invention.

FIG. 12A illustrates a bottom view of the ultrasound probe housing 104 having adhesion points 115 located across body side 114 of device 100 in accordance with another embodiment of the present invention. Adhesion points 115 are also holes 117 in this configuration and have no additional contouring on body side 114 of device 100. FIG. 12B provides a side cutaway view of ultrasound probe housing 104 in which adhesion points 115 and holes 117 are apparent and opened to body side 114. It will be appreciated that holes 117 and the corresponding architecture within ultrasound probe housing 104 may provide a source of adhesive instead of suction forces by which to fix device 100. FIG. 12B provides a side view cutaway for illustrate the exemplary architecture of ultrasound probe housing 104.

Figure 13A:
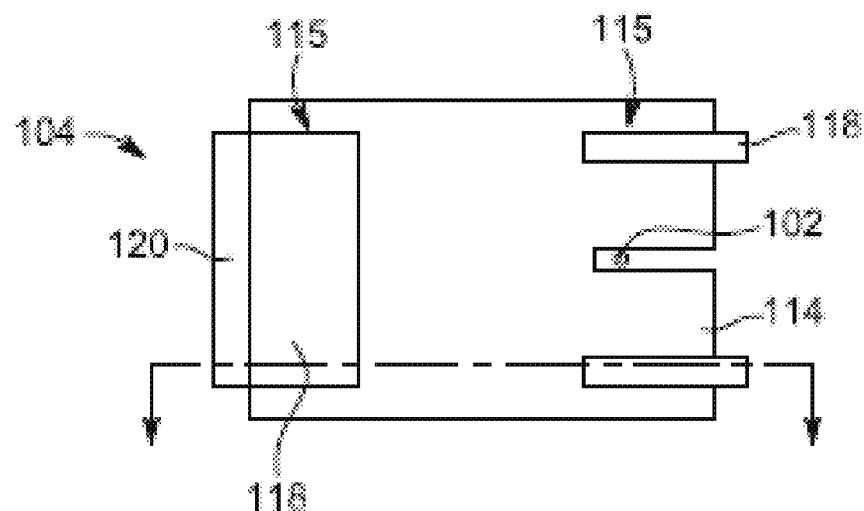
FIG. 13A illustrates a perspective view of the ultrasound probe housing having adhesion points located across the body side of the device in accordance with another embodiment of the present invention.
Figure 13B:
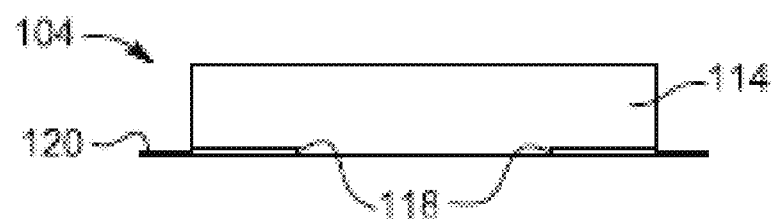
FIG. 13B illustrates a side view of ultrasound probe housing in which adhesion points and adhesive pads are apparent on body side of the device in accordance with another embodiment of the present invention.

FIG. 13A illustrates a bottom view of ultrasound probe housing 104 having adhesion points 115 located on body side 114 of device 100 in accordance with an embodiment of the present invention, where adhesion points 115 are ready for use adhesive pads or films 118. Adhesion points 115 may further contain a protective cover over adhesive pads or films 118 for storage that can be removed at time of use during the surgical procedure. It will be appreciated that body side 114 may be a receptacle for replaceable adhesive pads or films 118 that may be disposed of after each procedure. Such disposable adhesive pads or films 118 may be sterile. Ultrasound probe housing 104 may contain a removable cover 120 that coupleably joins all or a portion of body side 114. Removable cover 120 may itself provide adhesive pads or films 118 or the surface for adhesive pads or films 118 that can be fitted to body side 114 of device 100 for ease of use. Each removable cover 120 may be sterile and individually provided to ultrasound probe housing 104 for the specific procedure. FIG. 13B provides a side view of ultrasound probe housing 104 in which adhesion points 115 and adhesive pads or films 118 are apparent on body side 114.

Figure 14:
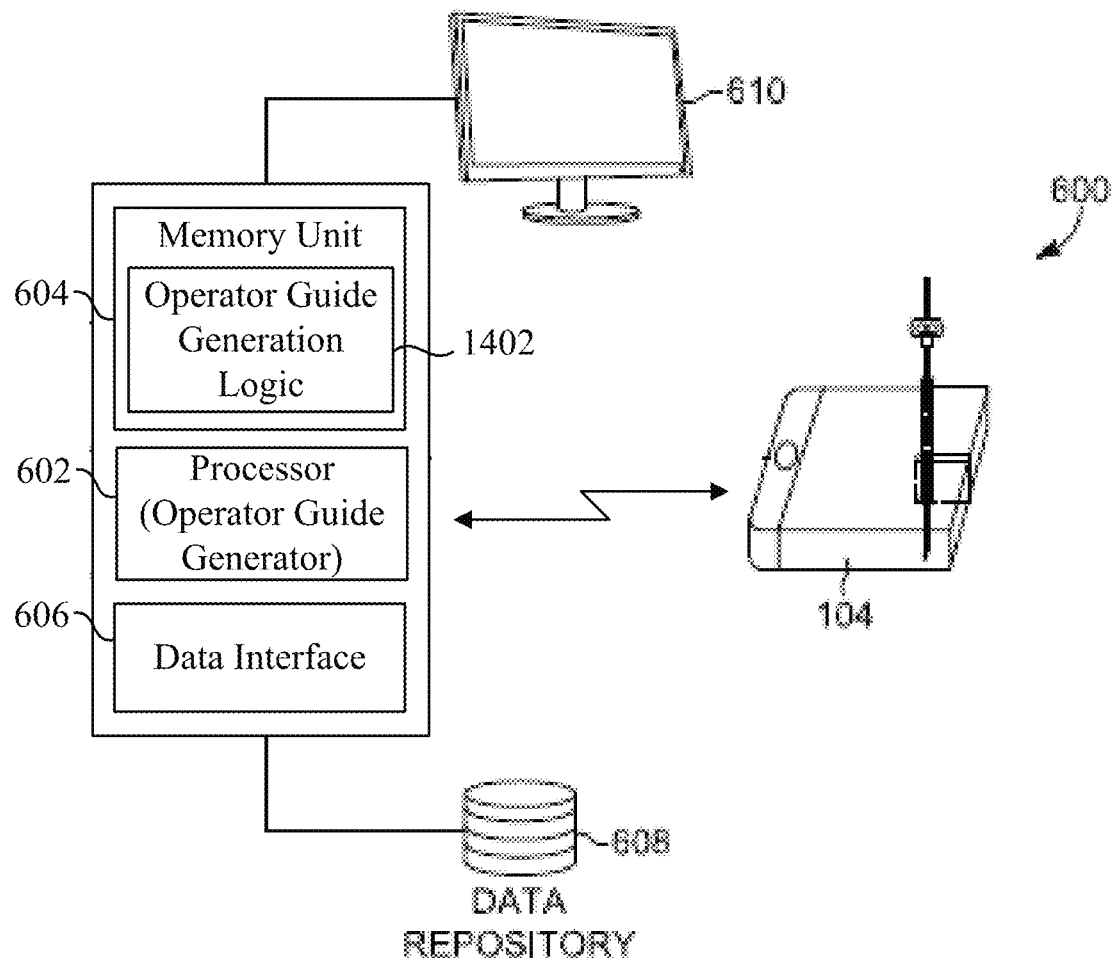
FIG. 14 illustrates a system for providing guidance to an operator of an ultrasound device in accordance with an embodiment of the present invention.

As discussed above in reference to FIGS. 6 and 7, in an embodiment, ultrasound probe housing 104 captures images of anatomical body parts 704 of patient 700 and such images are displayed on display unit 610 in real time (e.g., in 2D or 3D). Such images may be analyzed and modified by processor 602 prior to display by display unit 610. For example, FIG. 14 depicts an embodiment of system 600 in which ultrasound probe housing 104 is connected to data interface 606 via a wireless connection (although such connection may also be wired as noted above) and in which operator guide generation logic 1402 (e.g., computer code) is stored in memory unit 604 and executed by processor 602. The execution of operator guide generation logic 1402 by processor 602 causes processor 602 to act as an operator guide generator in a manner described herein. For example, the execution of operator guide generation logic 1402 by processor 602 may cause processor 602 to add to an image a visual overlay of or within a target site to aid visualization and guide an operator. In particular, through execution of operator guide generation logic 1402, processor 602 may determine an appropriate location for a visual overlay within an image based on available data and insert the overlay at the determined location. The available data may include, for example and without limitation, current real time data from device 100, stored data (e.g., reference data stored in data repository 608), and the type of procedure to be performed.

Figure 15A:
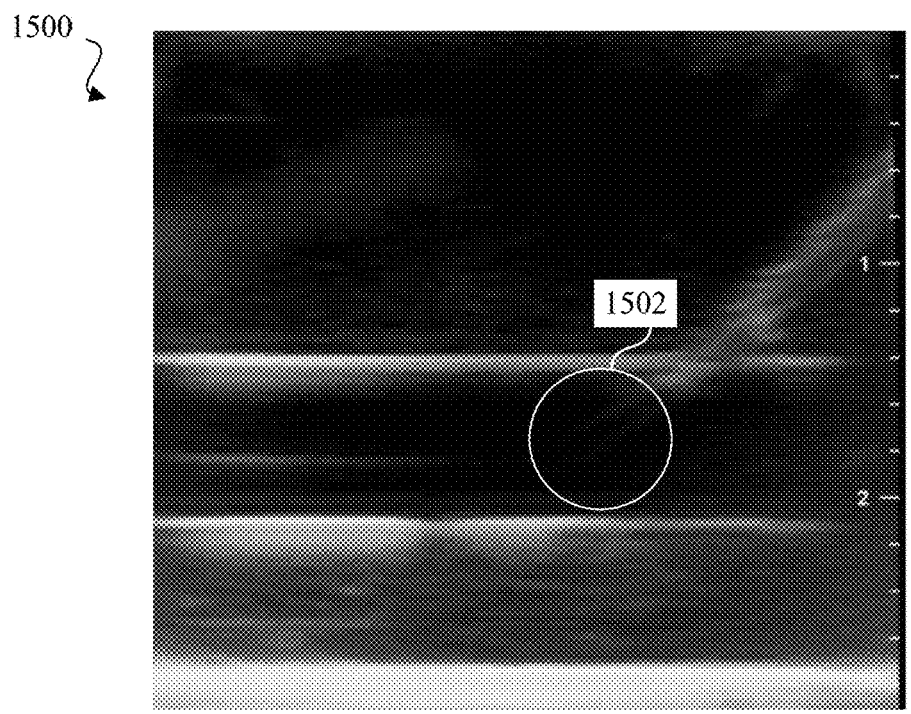
FIGS. 15A, 15B, 16A and 16B respectively illustrate an image that may be generated and displayed by the system of FIG. 14, in accordance with an embodiment of the present invention.

For example, FIG. 15A shows an example modified image 1500 that may be generated by processor 602 in a scenario in which ultrasound device 100 is being used to perform an intravenous (IV) cannula insertion and in which the target is a vessel lumen. In this example, processor 602 inserts a visual target overlay 1502 that would not otherwise appear in the image within the lumen diameter of the target vessel to help guide the operator. In the example of FIG. 15A, visual target overlay 1502 is partially transparent, and thus details of the original image can still be perceived beneath visual target overlay 1502. In another example, visual target overlay 1502 may be non-transparent or fluctuate between transparent and non-transparent, and may change color in response to operator action or processor 602.

Figure 15B:
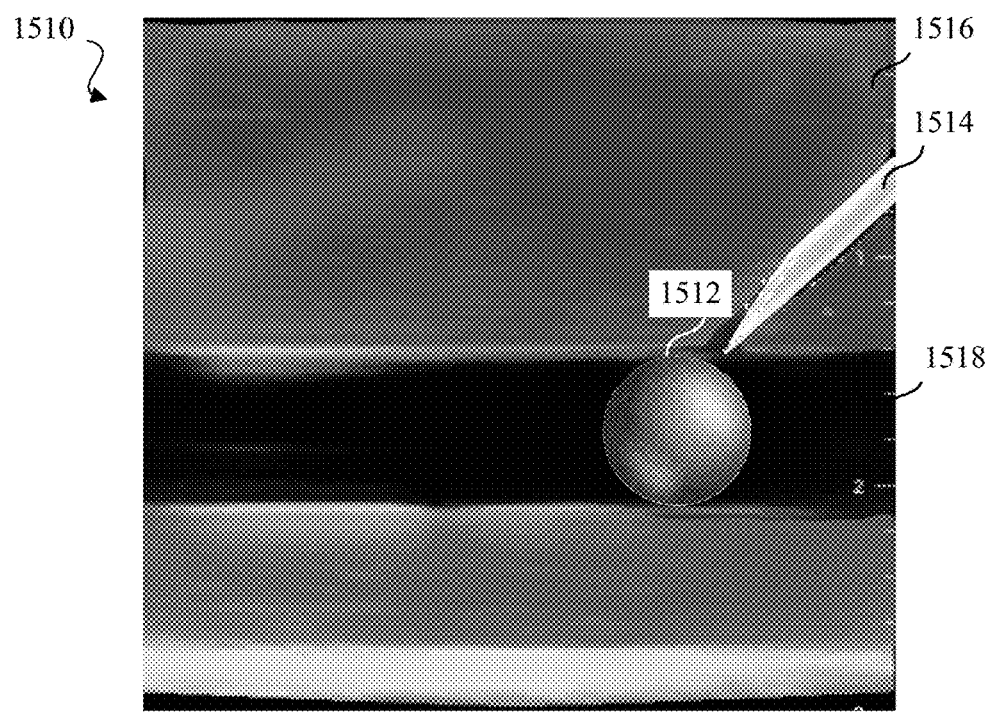

As another example, FIG. 15B shows an example modified image 1510 that may be generated by processor 602 in a similar scenario. In this example, processor 602 inserts a visual target overlay 1512 over the vessel lumen, a visual overlay 1514 over the needle, a visual overlay 1516 over tissue surrounding the blood vessel, and a visual overlay 1518 over the blood vessel itself. Different colors are used for the different visual overlays to help the operator distinguish between the different elements. In this example, it may be seen that the entire original image has, in a sense, been replaced by a visual overlay that is intended to help the operator in visualizing the anatomical body parts included within the image and in guiding the needle to the target location.

Figure 16A:
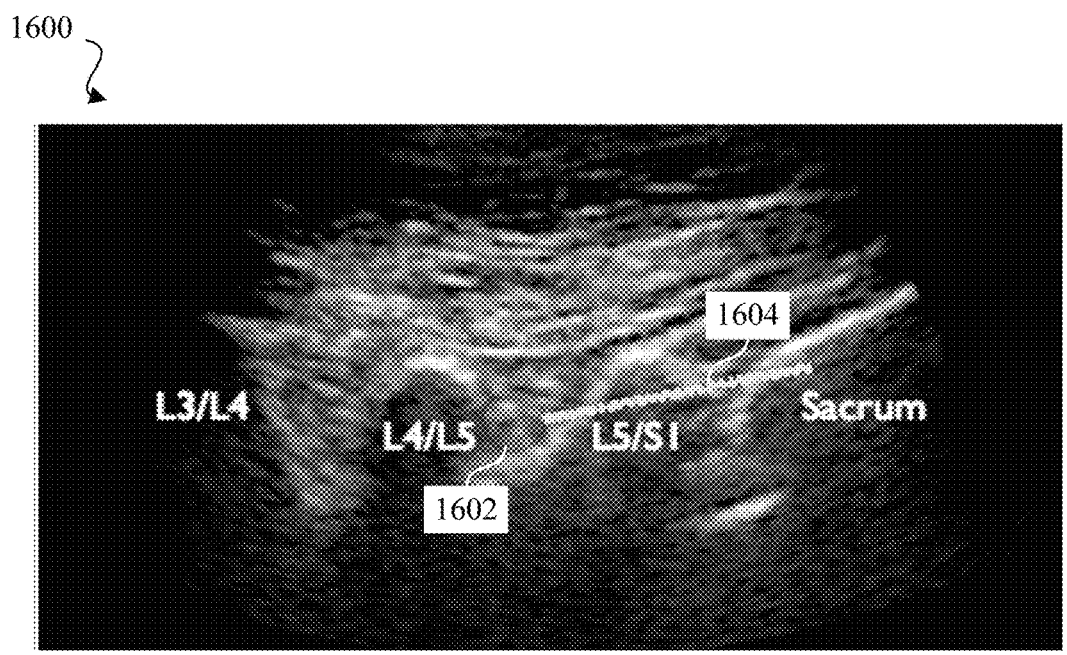

As yet another example, FIG. 16A shows an example modified image 1600 that may be generated by processor 602 in a scenario in which ultrasound device 100 is being used to perform a lumbar puncture and in which the target location is within the spinal canal between two lumbar bones. In this example, processor 602 inserts a visual target overlay 1602 that would not otherwise appear in the image within the spinal canal to help guide the operator. In the example of FIG. 16A, visual target overlay 1602 is partially transparent, and thus details of the original image can still be perceived beneath visual target overlay 1602. In this example, processor 602 also inserts a visual overlay 1604 that would not otherwise appear in the image over the needle.

Figure 16B:
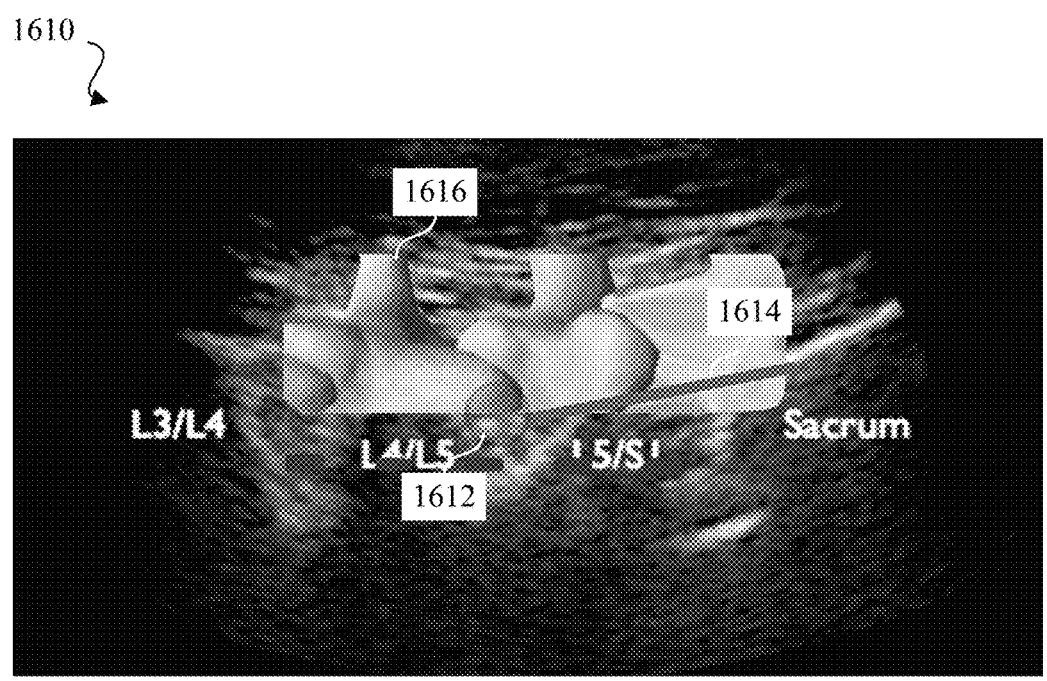

As yet another example, FIG. 16B shows an example modified image 1610 that may be generated by processor 602 in a similar scenario. In this example, processor 602 inserts a visual target overlay 1612 within the spinal canal, a visual overlay 1614 over the needle, and a visual overlay 1614 over the lumbar bones of the spine. Different colors are used for the different visual overlays to help the operator distinguish between the different elements.

In accordance with an embodiment, the visual target overlay may be color coded and processor 602 may be configured to change a color and/or intensity of the visual target overlay as an indicator of needle location relative to the target. The rendering of a visual target overlay in this manner can improve treatment outcomes by improving operator orientation and visualization of the target.

For example, with continued reference to FIG. 15A, as the operator's needle approaches visual target overlay 1502, processor 602 may cause visual target overlay 1502 to change color. As the operator's needle enters the target lumen, and thus visual target overlay 1502, processor 602 may indicate successful insertion within the target site by causing a further color change. For instance, processor 602 may cause visual target overlay 1502 to change from orange to green when the needle tip fully resides within the lumen of the target vessel. In a further embodiment, processor 602 may also cause an audible sound to be generated (e.g., via an integrated or attached speaker) to indicate successful insertion. Furthermore, processor 602 may be configured to indicate any deviation from the target site with the operator needle via a corresponding color change, and perhaps some other indicator (such as a corresponding audible sound), with the purpose of informing the operator that it has passed or missed the desired location. In accordance with an embodiment, a procedural outcome may entail an operator entering the target site and seeing the overlay as the proper color indicator, or other indicator, informing the operator to maintain the needle location. It will be appreciated that the target site can be any site within a patient's anatomy and that the visual overlay can be any shape or use any color or other indicator to identify successful (or unsuccessful) placement of the needle by the operator.

Processor 602 (through execution of operator guide generation logic 1402) may thus modify images captured by ultrasound probe housing 104 to improve needle visualization and location identification, thereby improving the chances of procedural success. For example, processor 602 may add a colored overlay to a needle represented in raw ultrasound image data. An example of this may be seen in FIG. 15B, in which the needle is highlighted with a colored visual overlay 1514. Processor 602 may further cause the needle overlay to change color depending on closeness to a target, or proximity to or alignment with a desired needle path. Processor 602 may indicate closeness to the target, for example, by using a color indicator like blue to green, or brightness level of a particular color. Processor 602 may also modify the raw ultrasound image data to show both the actual needle and its overlay, as well as a predicted needle overlay that maps ahead of the current needle location to a desired target site. In an embodiment, the system includes a user interface that enables an operator to toggle the system between raw image presentation and image presentation with overlays. For example, processor 602 may toggle between raw image presentation and image presentation with overlays responsive to an appropriate user input.

Processor 602 (through execution of operator guide generation logic 1402) may utilize color coding of the needle overlay to indicate needle depth, and/or may use some other visual, tactile, and/or audible indicator to provide information that is helpful to the operator, such as distance to target or direction to target. In an embodiment, processor 602 provides a countdown-type mechanism (e.g., 3 mm, 2 mm, 1 mm, at target) which can be conveyed in a convenient format like audibly or visually seen on a monitor (e.g., display unit 610). In one example, processor 602 may depict a countdown-type approach with needle progression to target by color coding depth in tissue surrounding the needle path. Tissue surrounding the tip of the needle or just before the tip of the needle may increase in color intensity, such as blue, as the needle enters that particular depth, and, as the needle passes that depth, tissue may transition back to raw image view or a different color or intensity. Processor 602 may also activate one or more tactile components in accordance with a non-intrusive approach, and such tactile indicator(s) can be used independently or in conjunction with other indicators of desired information. One example of tactile information might include a vibrational indicator relating to reaching the desired target site. For example, processor 602 may cause vibration of needle guide assembly 108 or other hand-held component of the operator's system, such as ultrasound probe housing 104. Tactile information may be conveyed apart from the procedural device and may be provided, for example, through a glove used during a procedure, or a finger ring or any other wearable that transmits the desired alert. Tactile indications can be used to provide any type of procedural information that may be relevant to the operator. In an embodiment, a system user can choose what information will give the tactile response. For example, a tactile response can be used to signal needle penetration, needle depth, needle path, target location, to name a few purposes. The signal indication can be unitary, extended, repetitive, intensity based, etc.

To help address the complexity of reading ultrasound images, processor 602 may provide a graphical overlay on received ultrasound images. Such rendering may be performed in real-time as the operator uses the ultrasound system, or can be prepared in advance based on prior ultrasound data from a patient. Processor 602 may be configured to vary opacity (e.g., in response to user input) between no identifiable overlay to complete overlay with an entire selectable range of opacity in between. In an embodiment, opacity adjustments can be made by the operator at any time via a suitable user interface. In a further embodiment, the user interface enables the system overlay to be toggled on or off in order to confirm fidelity to underlying raw data from the ultrasound procedure in order to assure the operator during the procedure. For example, an actuator to toggle between image states may be present on ultrasound probe housing 104. The system may be configured to offer any number of visual presentations such as a side-by-side view showing raw data in one visualization frame and a rendered frame in another. Processor 602 may be configured to enhance all parts of imaged environment or just select components, such as the needle and target.

Figure 17:
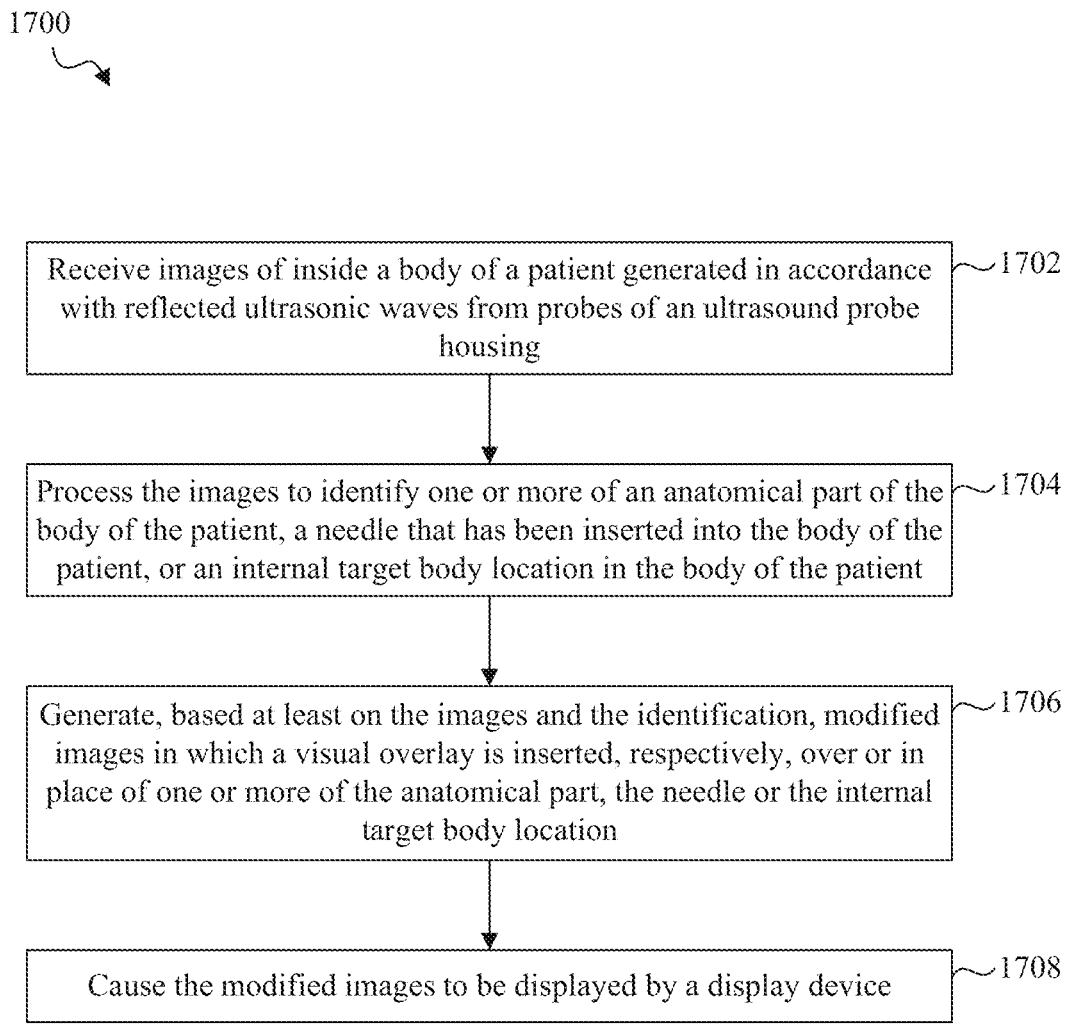
FIG. 17 illustrates a method for providing guidance to an operator of an ultrasound device in accordance with an embodiment of the present invention.

To further illustrate the foregoing features, FIG. 17 presents a flowchart 1700 of a method that may be performed by processor 602 responsive to execution of operator guide generation logic 1402. The method of flowchart 1700 may be used to guide an operator of an ultrasound device (e.g., device 100) when using such device to perform a needle insertion procedure.

As shown in FIG. 17, the method of flowchart 1700 begins at step 1702 in which processor 602 receives images of inside a body of a patient generated in accordance with reflected ultrasonic waves from probes (e.g., probes 105) of an ultrasound probe housing (e.g., ultrasound probe housing 104).

At step 1704, processor 602 processes the images to identify one or more of an anatomical part of the body of the patient, a needle that has been inserted into the body of the patient, or an internal target body location in the body of the patient. Processor 602 may identify these elements based on, for example and without limitation, current real time data from device 100, stored data (e.g., reference data stored in data repository 608), and/or the type of procedure to be performed.

At step 1706, processor 602 generates, based at least on the images and the identification, modified images in which a visual overlay is inserted, respectively, over or in place of one or more of the anatomical part, the needle or the internal target body location.

At step 1708, processor 602 causes the modified images to be displayed by a display device (e.g., display unit 610).

In an embodiment, the visual overlay associated with each of the anatomical part, the needle and the internal target body location is a different color.

In another embodiment, step 1706 of generating the modified images comprises changing an appearance of one or more of the visual overlay corresponding to the needle or the visual overlay corresponding to the internal target body location based on a distance or direction of the needle relative to the internal target body location, or changing an appearance of one or more of the visual overlay corresponding to the needle or the visual overlay corresponding to the anatomical part based on a distance or direction of the needle relative to the anatomical part. Changing the appearance of the visual overlay corresponding to the needle, the internal target body location, or the anatomical part of the body of the patient may comprise, for example, one or more of: changing a color of the visual overlay corresponding to the needle, the internal target body location, or the anatomical part of the body of the patient, or changing an intensity of the visual overlay corresponding to the needle, the internal target body location, or the anatomical part of the body of the patient.

In yet another embodiments, the method of flowchart 1700 may further include: causing the images and the corresponding modified images to be concurrently displayed by the display device (e.g., display unit 610); responsive to user input, toggling between causing the images to be displayed by the display device and causing the modified images to be displayed by the display device; or, responsive to user input, varying an opacity of the visual overlay corresponding to one or more of the anatomical part, the needle or the internal target body location.

In further embodiments, the method of flowchart 1700 may further include inserting a visual overlay corresponding to a desired path of the needle into the modified image. In further accordance with such an embodiment, the method may also include changing an appearance of one or more of the visual overlay corresponding to the needle or the visual overlay corresponding to the desired path of the needle based on a distance or direction of the needle relative to the desired path of the needle. Changing the appearance of the visual overlay corresponding to the needle or the desired path of the needle may comprise, for example, one or more of: changing a color of the visual overlay corresponding to the needle or the desired path of the needle, or changing an intensity of the visual overlay corresponding to the needle or the desired path of the needle.

In still further embodiments, step 1706 of generating the modified images further includes inserting a descriptive label corresponding to the anatomical part, the needle or the internal body part.

Figure 18:
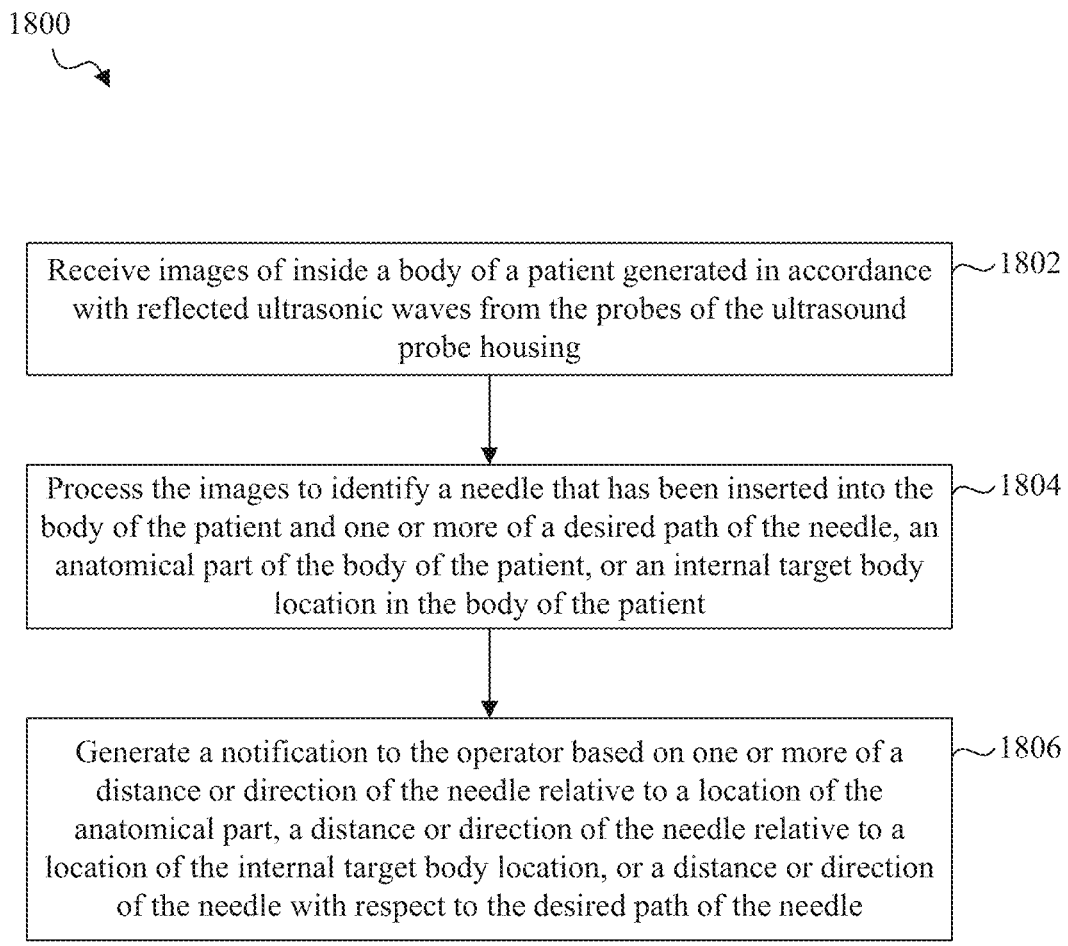
FIG. 18 illustrates another method for providing guidance to an operator of an ultrasound device in accordance with an embodiment of the present invention.

To help further illustrate the foregoing features, FIG. 18 presents a flowchart 1800 of a method that may be performed by processor 602 responsive to execution of operator guide generation logic 1402. The method of flowchart 1800 may be used to guide an operator of an ultrasound device (e.g., device 100) when using such device to perform a needle insertion procedure.

As shown in FIG. 18, the method of flowchart 1800 begins at step 1802 in which processor 602 receives images of inside a body of a patient generated in accordance with reflected ultrasonic waves from probes (e.g., probes 105) of an ultrasound probe housing (e.g., ultrasound probe housing 104).

At step 1804, processor 602 processes the images to identify a needle that has been inserted into the body of the patient and one or more of a desired path of the needle, an anatomical part of the body of the patient, or an internal target body location in the body of the patient. Processor 602 may identify these elements based on, for example and without limitation, current real time data from device 100, stored data (e.g., reference data stored in data repository 608), and/or the type of procedure to be performed.

At step 1806, processor 602 generates a notification to the operator based on one or more of a distance or direction of the needle relative to a location of the anatomical part, a distance or direction of the needle relative to a location of the internal target body location, or a distance or direction of the needle with respect to the desired path of the needle.

In an embodiment, the method of flowchart 1800 further includes generating modified images in which a visual overlay is inserted, respectively, over or in place of one or more of the needle, the desired path of the needle, the anatomical part, or the internal target body location. In further accordance with such an embodiment, generating the notification in step 1806 may comprise changing an appearance of one or more of the visual overlay corresponding to the needle, the visual overlay corresponding to the desired path of the needle, the visual overlay corresponding to the anatomical part, or the visual overlay corresponding to the internal target body location. Changing the appearance of one or more of the visual overlay corresponding to the needle, the visual overlay corresponding to the desired path of the needle, the visual overlay corresponding to the anatomical part, or the visual overlay corresponding to the internal target body location may comprise: changing a color or intensity of one or more of the visual overlay corresponding to the needle, the visual overlay corresponding to the desired path of the needle, the visual overlay corresponding to the anatomical part, or the visual overlay corresponding to the internal target body location.

In a further embodiment, generating the notification in step 1806 comprises generating an audible notification.

In a still further embodiment, generating the notification in step 1806 comprises generating a tactile indicator. In further accordance with such an embodiment, the tactile indicator may comprise, for example, a vibration of the ultrasound device (e.g., device 100 or ultrasound probe housing 104) or a component thereof (e.g., needle guide assembly 108), or a vibration of a wearable worn by the operator.

With respect to 2D versus 3D imaging, reference frame selection can provide additional value for the 2D environment. In one embodiment, processor 602 (through execution of operator guide generation logic 1402) enables continuous reference frame selection plus needle interpolation. For example, in an embodiment, an operator may provide input (via a suitable user interface) to processor 602 to select a desired frame of reference, and processor 602 may further allow for switching between frames of references with the primary limitation being the number of probes used to generate the raw data planal views. This frame of reference approach can also amplify received data using graphical overlays as discussed above. Using a frame of reference selection approach, the system can see gains in computational efficiency of more complicated data environments, like 3D imaging, and see gains generally in manipulation of the viewing environment.

It will be apparent that the environment, whether it be raw data viewed with reference frame selection or with graphical enhancements (or both), lends itself to a more automated procedural approach that may exclude a direct operator altogether or may allow an operator to work remotely with a virtual reality-type interface. Such interface might include tactile-based systems for operation and visual enhancement systems for remoted simulated viewing during real-time procedures. Embodiments can be used on standard viewing equipment and remote operator controls as well.

In another embodiment, processor 602 (through execution of operator guide generation logic 1402) also enables a user to select any number of vantage point views desired thereby. Conventional procedures are performed from a standard third-party view in which no one feature prevails from perspective, i.e., a flat view. For certain procedures, however, it may be desirable to have specific locked frame vantage points different from the flat view, such as that of the target, for improved operator function. In an example where the vantage point is that of the target, an operator's screen view or headset view will be from the target site looking outward. Approach of a needle will be viewed from the target itself as it closes in on the site. Alternatively, a vantage point might be that of the needle itself, akin to the view of a camera scope used in other medical procedures. An embodiment may provide several preselected vantage points per procedure for the operator to select prior to or during the procedure itself. As with other selectable features, an embodiment may allow the operator to toggle between vantage points as desired.

Figure 19:
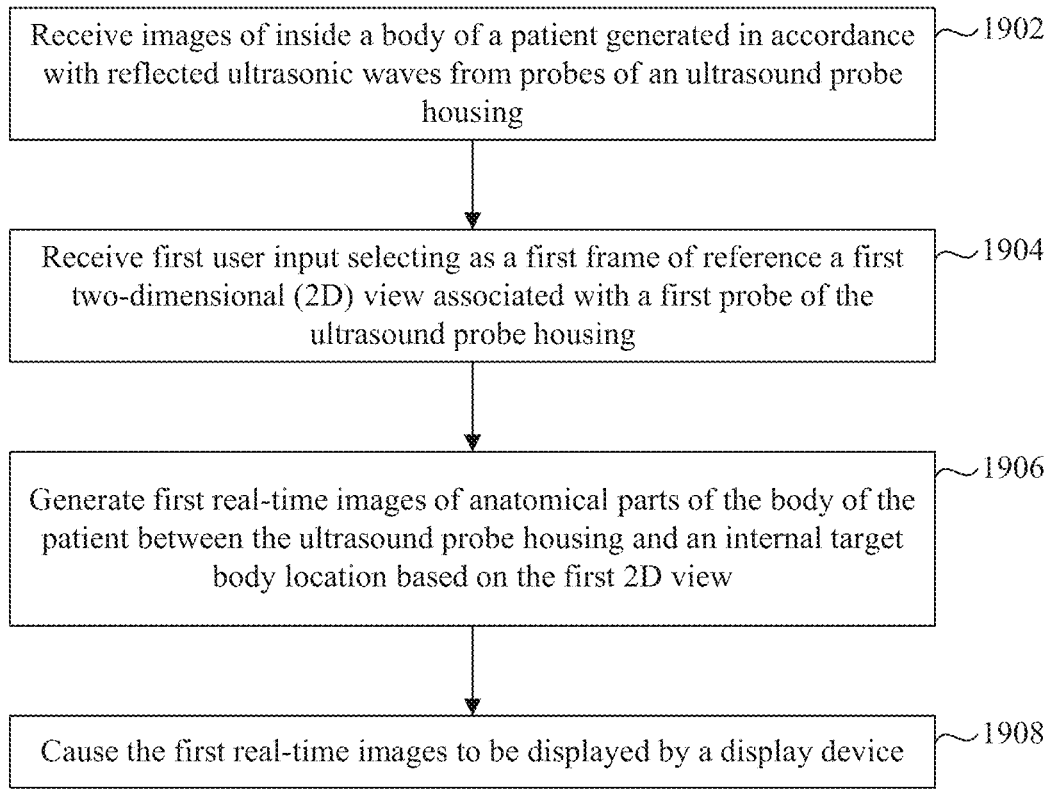
FIG. 19 illustrates a further method for providing guidance to an operator of an ultrasound device in accordance with an embodiment of the present invention.

To further illustrate the foregoing features, FIG. 19 presents a flowchart 1900 of a method that may be performed by processor 602 responsive to execution of operator guide generation logic 1402. The method of flowchart 1900 may be used to guide an operator of an ultrasound device (e.g., device 100) when using such device to perform a needle insertion procedure.

As shown in FIG. 19, the method of flowchart 1900 begins at step 1902 in which processor 602 receives images of inside a body of a patient generated in accordance with reflected ultrasonic waves from probes (e.g., probes 105) of an ultrasound probe housing (e.g., ultrasound probe housing 104).

At step 1904, processor 602 receives first user input selecting as a first frame of reference a first 2D view associated with a first probe of the ultrasound probe housing.

At step 1906, processor 602 generates first real-time images of anatomical parts of the body of the patient between the ultrasound probe housing and an internal target body location based on the first 2D view.

At step 1908, processor 602 causes the first real-time images to be displayed by a display device (e.g., display unit 610).

Figure 20:
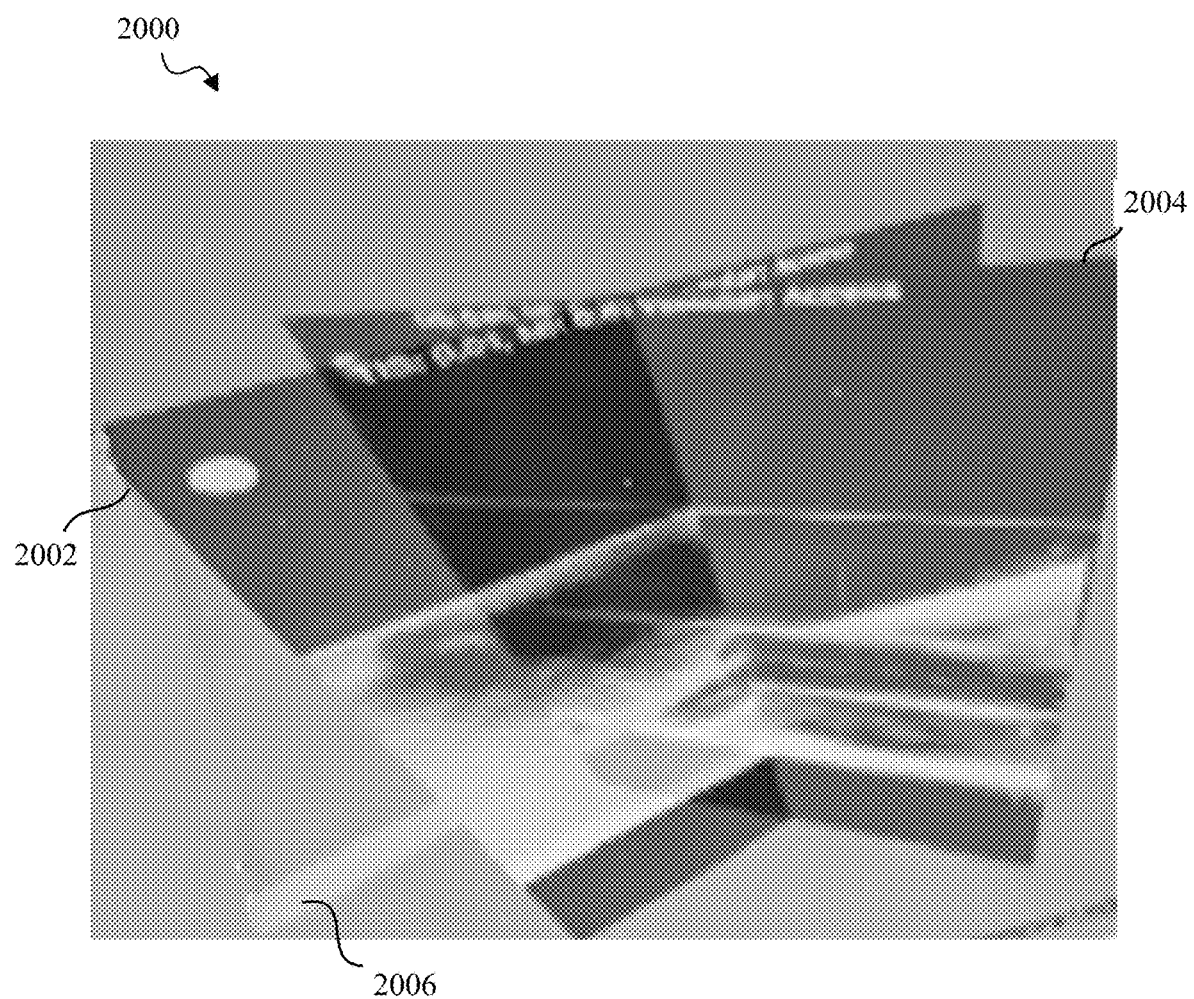
FIG. 20 illustrates a simulated 3D ultrasound image that may be generated from a replicated 2D ultrasound image in accordance with an embodiment of the present invention.

In an embodiment, step 1906 is performed by replicating the first 2D view to generate a replicated first 2D view and then combining the first 2D view and the replicated first 2D view to generate a simulated 3D image. An example of this is shown in FIG. 20, which shows how a first 2D view 2002 that is associated with a first probe of the ultrasound probe housing can be replicated to create a replicated first 2D view 2004, and how those two views can then be combined to generate a simulated 3D image. In further accordance with such an embodiment, step 1906 may further be performed by determining a location of a needle present in the first 2D view and the replicated first 2D view and then utilizing interpolation to display the needle within the simulated 3D view. An example of this is also shown in FIG. 2, wherein interpolation is used to display needle 2006 within the simulated 3D view.

In a further embodiment, the method of flowchart 1900 may further include the performance of the following steps by processor 602: receiving second user input selecting as a second frame of reference a second 2D view associated with a second probe of the ultrasonic probe housing; generating second real-time images of anatomical parts of the body of the patient between the ultrasound probe housing and an internal target body location based on the second 2D view; and causing the second real-time images to be displayed by the display device. In further accordance with such an embodiment, causing the second real-time images to be displayed by the display device comprises: causing the first real-time images and the second real-time images to be concurrently displayed by the display device.

In the foregoing description, it will be readily appreciated by those skilled in the art that modifications may be made to the invention without departing from the concepts disclosed herein. Such modifications are to be considered as included in the following claims, unless the claims by their language expressly state otherwise.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. The various embodiments set forth herein are described in terms of exemplary block diagrams and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment.

What is claimed is:

1. A system, comprising:
   an ultrasound device comprising an ultrasound probe housing that contains a plurality of probes;
   at least one processor connected with the ultrasound device through a data interface and further connected to a display device; and
   at least one memory unit that stores instructions for processing by the processor, the instructions being configured to cause the processor to:
      receive images of inside a body of a patient generated in accordance with reflected ultrasonic waves from the probes of the ultrasound probe housing;
      process the images to identify therein a needle that has been inserted into the body of the patient and one or more of an anatomical part of the body of the patient or a target internal body part in the body of the patient;
      generate, based at least on the images and the identification, modified images by adding a first visual overlay over or in place of the needle, and by one or more of (i) adding a second visual overlay over or in place of the anatomical part or (ii) adding a third visual overlay over or in place of the internal target body part; and
      cause the modified images to be displayed by the display device.

2. The system of claim 1, wherein the first visual overlay is a different color than one or more of the second visual overlay or the third visual overlay.

3. The system of claim 1, wherein the instructions are configured to cause the processor to generate the modified images by adding the first visual overlay over or in place of the needle, adding the third visual overlay over or in place of the target internal body part, and changing an appearance of one or more of the first visual overlay or the third visual overlay based on a distance or direction of the needle relative to the internal target body location.

4. The system of claim 3, wherein changing the appearance of one or more of the first visual overlay or the third visual overlay comprises at least one of:
   changing a color of one or more of the first visual overlay or the third visual overlay; or
   changing an intensity of one or more of the first visual overlay or the third visual overlay.

5. The system of claim 1, wherein the instructions are further configured to cause the processor to:
   cause one of the images and a corresponding one of the modified images to be concurrently displayed by the display device.

6. The system of claim 1, wherein the instructions are further configured to cause the processor to:
   responsive to user input, toggle between causing the images to be displayed by the display device and causing the modified images to be displayed by the display device.

7. The system of claim 1, wherein the instructions are further configured to cause the processor to:
   responsive to user input, vary an opacity of the first visual overlay, the second visual overlay or the third visual overlay.

8. The system of claim 1, wherein the instructions are further configured to cause the processor to generate the modified images by:
   adding a fourth visual overlay that represents a desired path of the needle into the modified image.

9. The system of claim 8, wherein the instructions are further configured to cause the processor to generate the modified images by:
   changing an appearance of one or more of the first visual overlay or the fourth visual overlay based on a distance or direction of the needle relative to the desired path of the needle.

10. The system of claim 1, wherein the instructions are further configured to cause the processor to generate the modified images by:
 inserting a descriptive label corresponding to the anatomical part, the needle or the internal body part.

11. The system of claim 1, wherein the instructions are configured to cause the processor to generate the modified images by adding the first visual overlay over or in place of the needle, adding the second visual overlay over or in place of the anatomical part, and changing an appearance of one or more of the first visual overlay or the second visual overlay based on a distance or direction of the needle relative to the anatomical part.

12. The system of claim 11, wherein changing the appearance of one or more of the first visual overlay or the second visual overlay comprises at least one of:
 changing a color of one or more of the first visual overlay or the third visual overlay; or
 changing an intensity of one or more of the first visual overlay or the third visual overlay.

13. A method for providing guidance to an operator of an ultrasound device that comprises an ultrasound probe housing that contains a plurality of probes, the method comprising:
 receiving images of inside a body of a patient generated in accordance with reflected ultrasonic waves from the probes of the ultrasound probe housing;
 processing the images to identify within the images at least a needle that has been inserted into the body of the patient; and
 generating a notification to the operator based on one or more of:
  a distance or direction of the needle relative to a location of an anatomical part of the body of the patient;
  a distance or direction of the needle relative to a location of a target internal body part in the body of the patient; or
  a distance or direction of the needle relative to a location of a desired path of the needle.

14. The method of claim 13, further comprising:
 generating modified images in which a visual overlay is added over or in place of the needle; and
 wherein generating the notification comprises changing an appearance of the visual overlay.

15. The method of claim 14, wherein changing the appearance of the visual overlay comprises:
 changing a color or intensity of the visual overlay.

16. The method of claim 13, wherein generating the notification comprises generating an audible notification.

17. The method of claim 13, wherein generating the notification comprises generating a tactile indicator.

18. The method of claim 17, wherein the tactile indicator comprises a vibration of the ultrasound device or a component thereof or of a wearable worn by the operator.

19. The method of claim 13, wherein processing the images comprises processing the images to identify at least the needle and the anatomical part, wherein the notification to the operator is generated based on the distance or direction of the needle relative to the location of the anatomical part, and wherein the method further comprises:
 generating modified images in which a visual overlay is added over or in place of the anatomical part; and
 wherein generating the notification comprises changing an appearance of the visual overlay.

20. The method of claim 13, wherein processing the images comprises processing the images to identify at least the needle and the target internal body part, wherein the notification to the operator is generated based on the distance or direction of the needle relative to the location of the target internal body part, and wherein the method further comprises:
 generating modified images in which a visual overlay is added over or in place of the target internal body part; and
 wherein generating the notification comprises changing an appearance of the visual overlay.

21. The method of claim 13, wherein processing the images comprises processing the images to identify at least the needle and the desired path of the needle, wherein the notification to the operator is generated based on the distance or direction of the needle relative to a location of the desired path of the needle, and wherein the method further comprises:
 generating modified images in which a visual overlay is added over or in place of the desired path of the needle; and
 wherein generating the notification comprises changing an appearance of the visual overlay.

* * * * *

UNITED STATES PATENT AND TRADEMARK OFFICE
CERTIFICATE OF CORRECTION

PATENT NO. : 11,877,888 B2
APPLICATION NO. : 18/164294
DATED : January 23, 2024
INVENTOR(S) : Adams et al.

It is certified that error appears in the above-identified patent and that said Letters Patent is hereby corrected as shown below:

In the Claims

In Column 20, Claim 1, Line 18, delete "internal target" and insert -- target internal --, therefor.

Signed and Sealed this
Fifteenth Day of October, 2024

Katherine Kelly Vidal
*Director of the United States Patent and Trademark Office*